United States Patent [19]
Holt et al.

[11] Patent Number: 5,677,125
[45] Date of Patent: Oct. 14, 1997

[54] METHOD OF DETECTION AND DIAGNOSIS OF PRE-INVASIVE CANCER

[75] Inventors: Jeffrey T. Holt; Roy A. Jensen, both of Franklin; David L. Page, Nashville; Patrice S. Obermiller, Nashville; Cheryl L. Robinson-Benion, Nashville, all of Tenn.

[73] Assignee: Vanderbilt University, Nashville, Tenn.

[21] Appl. No.: 182,961

[22] Filed: Jan. 14, 1994

[51] Int. Cl.$^6$ .............................. C12P 19/34; C12Q 1/68
[52] U.S. Cl. .............................. 435/6; 435/91.2; 935/77; 935/78
[58] Field of Search ................. 435/6, 91.2; 935/77, 935/78

[56] References Cited

FOREIGN PATENT DOCUMENTS 0284362  9/1988  European Pat. Off. .............. 435/6

OTHER PUBLICATIONS

Holt JT, RA Jensen, and DL Page. Histopatholoy: Old Principles and new methods. 1994. Cancer Surveys. vol. 18: A New Look at Breast Cancer.

Liang P, and AB Pardee. 1992. Differential display of eukaryotic mRNA by means of the polymerase chain reaction. Science 257:967–971.

Sanchez LM, F Vizoso, I Diez–Itza, C Lopez–Otin. 1992. Cancer Res 32:95–100.

Dupont WD, and DL Page. 1985. Risk factors for beast cancer in women with proliferative breast disease. N.Engl-.J.Med. 312:146–151.

Davis et al., Basic Methods in Molecular Biology, Elsevier, NY 1986 pp. 276–284.

Kang et al. Science 229:974–978 (1985).

Marx, Science 244:654–655 (12 May 1989).

Slamon et al., Science 244:256–262 (12 May 1989).

Singleton et al., Dictionary Microbiology and Molecular Biology (1987) pp. 783, 889, 890.

*Primary Examiner*—Stephanie W. Zitomer
*Attorney, Agent, or Firm*—Waddey & Patterson; Mark J. Patterson; Arles A. Taylor, Jr.

[57] ABSTRACT

The present invention provides a method of detecting and diagnosing pre-invasive breast cancer by identifying differentially expressed genes in early, pre-invasive breast cancer tissue. Differentially expressed genes can be used as genetic markers to indicate the presence of pre-invasive cancerous tissues. Microscopically-directed tissue sampling techniques combined with differential display or differential screening of cDNA libraries are used to determine differential expression of genes in the early stages of breast cancer. Differential expression of genes in preinvasive breast cancer tissue is confirmed by RT-PCR, nuclease protection assays and in-situ hybridization of ductal carcinoma in situ tissue RNA and control tissue RNA.

22 Claims, 9 Drawing Sheets
(3 of 9 Drawings in Color)

Figure 1:

Table I: Anatomic Lesion Types in the Human Breast with Pre-malignant Implication

| Pre-malignant Lesions | Relative Risk* | p value | Reference |
|---|---|---|---|
| Indicators of generalized increased risk | | | |
| Atypical ductal hyperplasia | 4-5 fold | <0.00001 | (Dupont, et al, 1985 and 1993 |
| Lobular CIS | 9-10 fold | <0.00001 | Page, et al, 1991 |
| Determinant Lesions with Regional Risk | | | |
| Non-comedo DCIS | 10-11 fold | <0.00005 | Page, et al, 1991 |

* Represents the 95% confidence interval for relative risk.

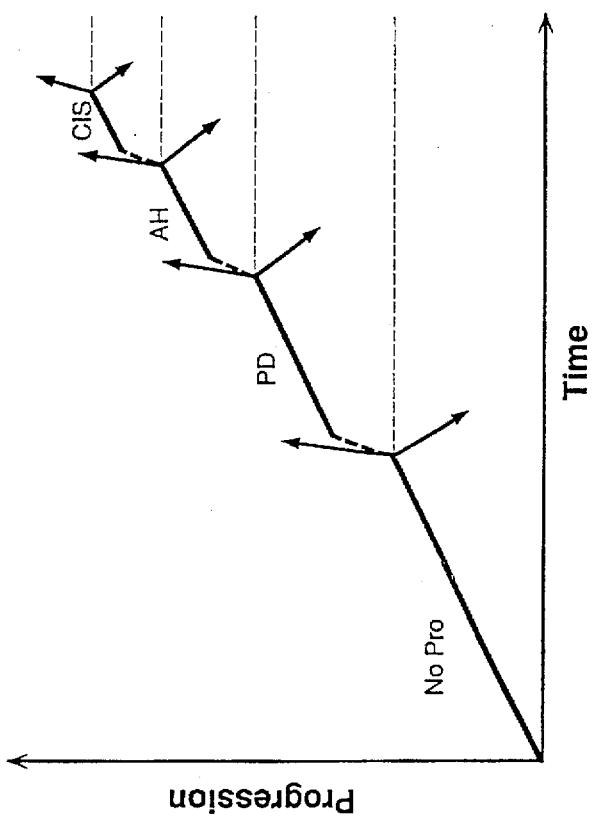

Figure 2: Model for premalignant conditions, highlighting magnitude of risk for progression to clinical malignancy. Terms from human breast neoplasia are used:

No Pro = no proliferative disease
PDWA = proliferative disease without atypia
AH = typical hyperplasia
CIS = carcinoma in situ As is the proposal of tumor progression each stage is more likely to proceed to the next (dotted lines), but could also remain stable (horizontal lines, probably fairly frequent), or directly proceed to develop a clone of cells with malignant behavior (vertical lines, becoming more likely further to right.)

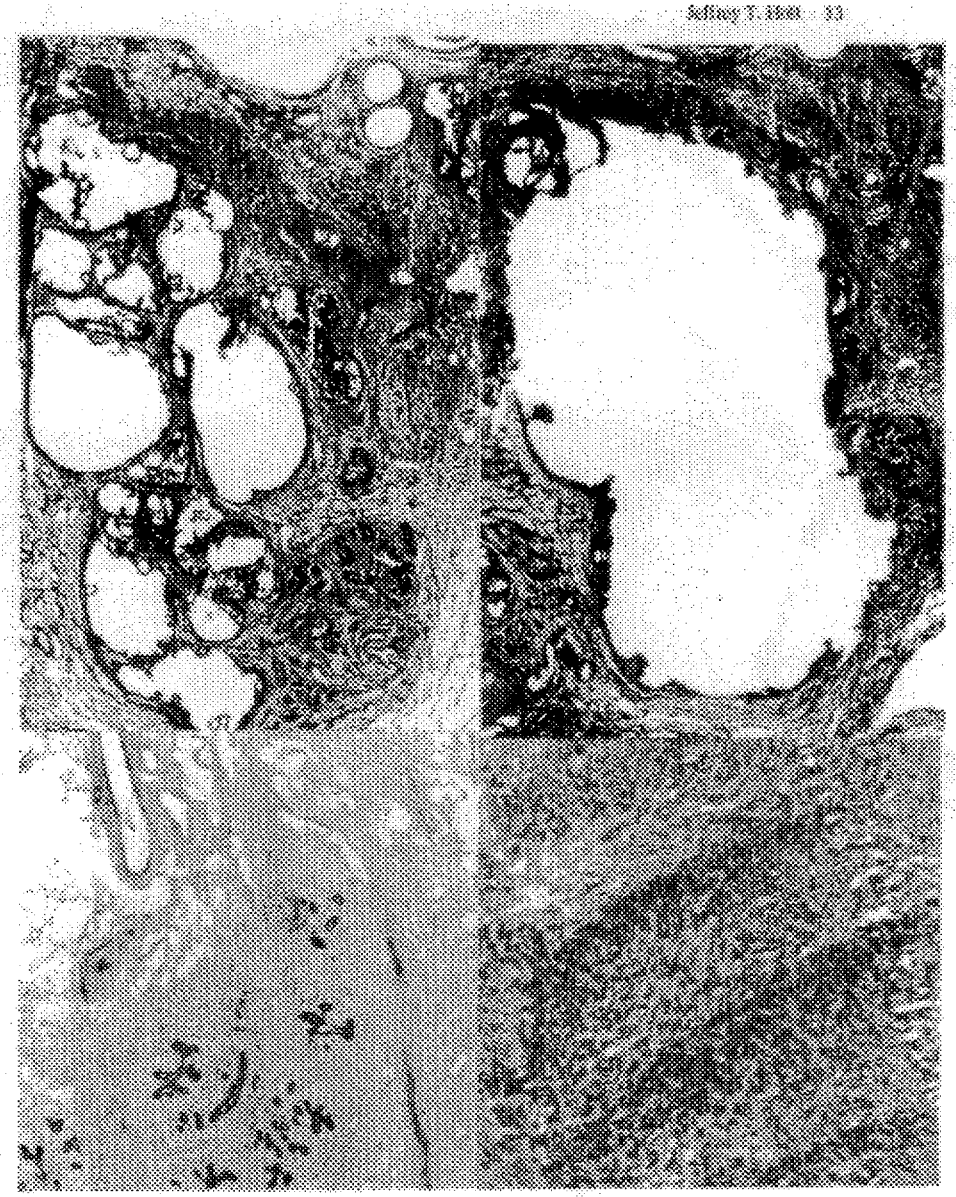
Figure 3: Photographs of DCIS tissue, before (upper left panel) and after excisional punch biopsy (upper right panel). The lower panels show tissue samples of normal breast tissue (lower left panel), and invasive breast cancer (lower right panel).

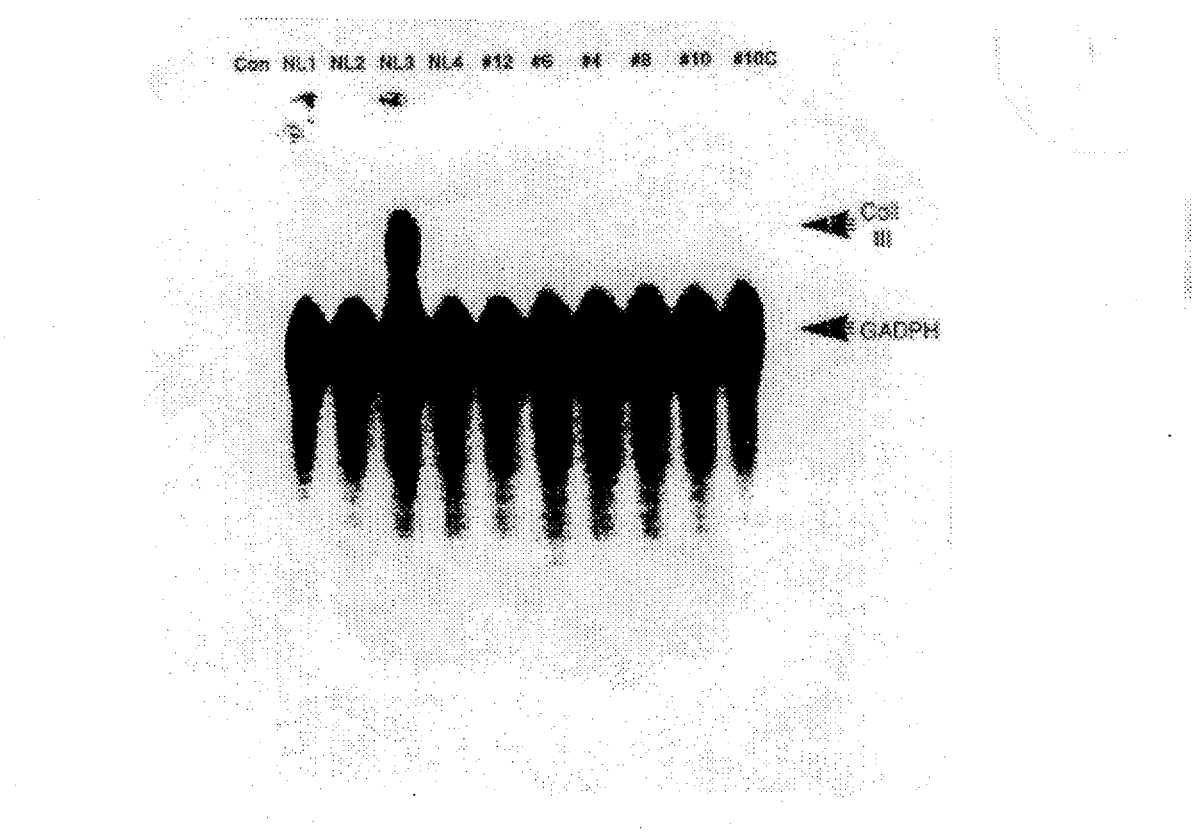

Figure 4: Expression of Collagen III mRNA in tissue mRNA samples was analyzed by RNase protection assay by methods we have reported previously (Holt, 1993). One ug of mRNA was hybridized with two labeled RNA probes: a T7 polymerase-generated probe for human glyceraldehyde phosphate dehydrogenase (GADP) which protects a 140 bp Sac I-Xba I fragment; and a T7 polymerase-generated probe which protects a 208 bp Hinc II-Pst I fragment from the 3' untranslated region of the human type III procollagen gene (Coll III) obtained by PCR subcloning the published sequence (Ala-Kokko, 1991). RNA samples were labeled as follows: NL1 is RNA from cultured human breast epithelial cells (Hammond et al, 1984), NL2 is RNA from normal breast tissue, NL3 is RNA derived from the fibrous stromal fraction of breast tissue as described (Jensen et al, submitted for publication). NL4 is another sample from normal breast tissue. #12, #8, #4, #6, and #10 are from patient samples with DCIS. Sample #10CA is RNA obtained from the small focus of microinvasion shown in Figure 3 in the upper right panel. Con is a control sample using tRNA.

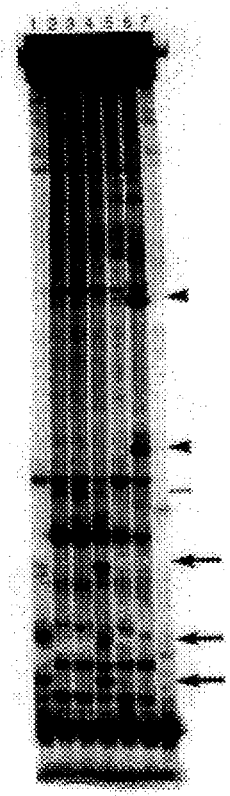

Figure 5: Differential Display of cDNAs obtained from patient tissue samples and controls. Rescued cDNA library samples were used as templates for low stringency PCR with the primers 5' GATGAGTTCGTGTCCGT ACAACTGG- 3' and 5' GGTTATCGAAATCAGCCACAGCGCC; 40 cycles were performed with denaturation for 1 minute at 94° C., annealing for 2 minutes at 25° C., and extension for 1 minute at 72° C. The samples correspond to those in the legend to Figure 5: Lane 1 is #12; Lanes 2 and 3 are from separate phage rescues of NL1 to show reproducibility of the assay; Lane 4 is #8; Lane 5 is #10; Lane 6 is #10CA; Lane 7 is a control from the rescued phage vector without cDNA inserts. Arrows mark cDNAs which are overexpressed in DCIS versus normal and arrowheads mark cDNAs which are differentially expressed in the invasive cancer (note this may reflect contamination from stromal cells as shown in Figure 3). The bar marks a cDNA which is expressed in normal breast cells at higher levels than in DCIS or invasive cancer.

Figure 6  Comparison of the sequence between DCIS-1 [SEQ ID NO: 1] and the human and hamster genes.

```
Human    TTCTCCTGACCACTAATGGGAGCCAATTCACAATTCAC
         ||| ||||| |||||| ||||||||| ||| |||
Hamster  TTCTGTTCACCACTGATGGCCAGCTAATGAA-AATGC--

Human    TAAGTGACTAAAGTAAAGTTAAACTTGTGTAGACTAAGCAT
         ||||| |||||||    |||||   |||        |||||
Hamster  -AAGTGACTCAG---AAGTTA----GTGTT-----AGCAT DCIS-1   GGGGGATCCACTAGTTC-AGAGCAGGCCCGCCACCCG
         |||||||||||||||||  ||||  ||| ||||||||
Hamster  GGGGGATCCACTAGTTCTAGAGCGG-CCGCCACCGC DCIS-1   TAGGACTCCAGCTTTTGTTCCCTCTAGTGAAGGGTTAA
         | |||||||||||||||||||||  |||||| ||||||
Hamster  TGGAGCTCCAGCTTTTGTTCCCTTTAGTGA-GGGTTAA
```

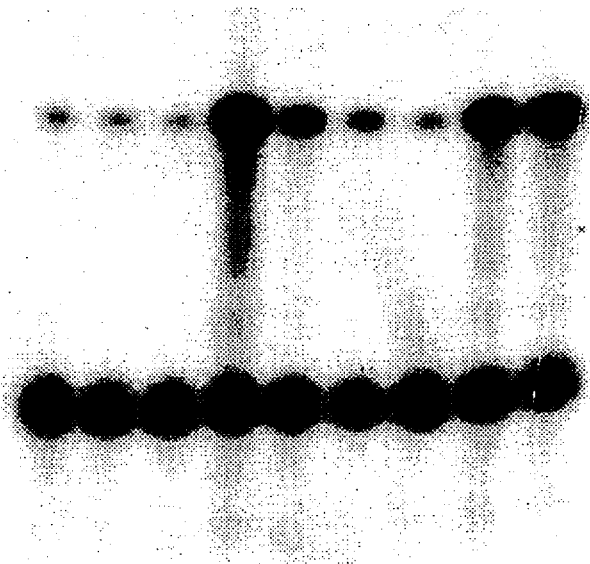
Figure 7: Expression of DCIS-1 mRNA in tissue mRNA samples analyzed by RNase protection assay as described in the legend to Figure 3. We used the GADH probe and a probe for the clone DCIS-1 which was generated by linearizing the rescued plasmid with Pvu II and should generate a 200 bp protected fragment. RNA samples were labeled as in the legend to Figure 4.

Figure 8: Table 2 - the Genetic Code

| Amino Acid | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | T | UAC | UAU | | | | |

FIGURE 9

TABLE OF DIFFERENTIALLY EXPRESSED MARKER GENES FROM PRE-INVASIVE HUMAN BREAST TISSUE

SEQ ID NO: 1: (DCIS-1)

| | |
|---|---|
| TTGGGAATTG GGTACGCGGG CCCCCCACTG TGCCGAATTC CTGCATGCGG GGGATCCACT | 60 |
| AGTTCAGAGC CCGTAGGACT CCAGCTTTTG TCGTTCCCTT TAGTGAGGGT TAATTTTCGA | 120 |
| GCTTGGCGTA ATCATGGTCA TCCTGTGTGA AATTGTTATC CGCTCACAAT TCCACACAAC | 180 |
| ATACGAGCCG GAAGCATAAA AGTGTAAGCA ATGAGTGAGC TAACTCACAT TAA | 233 |

SEQ ID NO: 2: (DCIS-2)

| | |
|---|---|
| TAGCCCGGTT ATCGAAATAG CCACAGCGCC TCTTCACTAT CAGCAGTACG CCGCCCAGTT | 60 |
| GTACGGACAC GG | 72 |

SEQ ID NO: 3: (DCIS-3)

| | |
|---|---|
| TGCCCGATGA GTTGTGTCGT ACAACTGGCG CTGTGGCTGA TTTCGATAA | 49 |

SEQ ID NO: 4: (DCIS-4)

| | |
|---|---|
| TAGCCCATGA GTTCGTGTCC GTACAACTGG GGCGCTGTGG CTGATTTCGA TANNNNNAGC | 60 |
| ATCAGCCCGA CG | 72 |

SEQ ID NO: 5: (DCIS-5)

| | |
|---|---|
| TAGCCCGGTT ATCGAAATCA GCCACAGCGC CTAACTTCTG CAGAAGCCTT TGACCATCAC | 60 |
| CAGTTGTACG GAAACGAACT CATC | 84 |

SEQ ID NO: 6: (DCIS-6)

| | |
|---|---|
| GTGGTTTCCG AAATTCCTGG GAAGGGGGGT GCTGGCGTGT GGAATTGTCG CGGCCCCTGG | 60 |
| TCTGCCGCGG CGTTTTTTGT CTACATTCGTC GTAGCTCG | 98 |

SEQ ID NO: 7: (DCIS-7)

| | |
|---|---|
| ATCAGCGCGC GACATTCGGG TACCCGCGCC C*****TCCG TCGGAATTCC TCGAGCCGGG | 60 |
| AT**ATAGGA TGTGGAGTTA GTTTTGTT | 88 |

METHOD OF DETECTION AND DIAGNOSIS OF PRE-INVASIVE CANCER

This invention was made in part from government support under Grant No. ES-00267 from the National Institutes of Health, National Institute of Environmental Health Sciences. The government has certain rights in the invention.

UTILITY STATEMENT

The detection of differentially expressed genes in pre-invasive breast tissue, specifically in non-comedo ductal carcinoma in situ as compared to genes expressed in normal tissue, is useful in the diagnosis, prognosis and treatment of human breast cancer. Such differentially expressed genes are effective marker genes indicating the significantly increased risk of breast cancer in a patient expressing these differentially expressed marker genes. These marker genes are useful in the detection, early diagnosis, and treatment of breast cancer in humans.

ACTIVITY STATEMENT

Of the differentially expressed genes described in this invention, DCIS-1 encodes a gene similar to the M2 subunit of hamster ribonucleotide reductase. The M2 subunit of ribonucleotide reductase (RibRed, hereafter) is responsible for regulation of RibRed. The differential levels of expression of the marker genes described in this invention (Seq ID Nos. 1–7), indicate genetic changes which have been linked to the presence of pre-invasive breast cancer.

BACKGROUND OF THE INVENTION

1. Technical Field

The present invention relates generally to methods of detection and diagnosis of breast cancer and more particularly to a diagnostic method which relies on the identification of marker genes expressed in pre-invasive cancers by microscopically-directed cloning. Furthermore, this invention concerns the prevention, detection, and diagnosis of breast cancer by addressing the molecular events which occur during the earliest alterations in breast tissue.

2. Description of the Prior Art

It will be appreciated by those skilled in the art that there exists a need for a more sensitive and less invasive method of early detection and diagnosis of breast cancer than those methods currently in use. Breast cancer presents inherent difficulties in regard to the ease with which it is detected and diagnosed. This is in contrast to detection of some other common cancers, including skin and cervical cancers, the latter of which is based on cytomorphologic screening techniques.

There have been several attempts to develop improved methods of breast cancer detection and diagnosis. In the attempts to improve methods of detection and diagnosis of breast cancer, numerous studies have searched for oncogene mutations, gene amplification, and loss of heterozygosity in invasive breast cancer (Callahan, et al., 1992; Cheickh, et al., 1992; Chen, et al, 1992; and Lippman, et al, 1990). However, few studies of breast cancer have analyzed gene mutations and/or altered gene expression in ductal carcinoma in situ (DCIS). Investigators have demonstrated high levels of p53 protein in 13–40% of DCIS lesions employing a monoclonal antibody to p53, and subsequent sequencing demonstrated mutations in several cases (Poller et al, 1992). The neu/erbB2 gene appears to be amplified in a subset of DCIS lesions (Allred et al, 1992; Maguire et al, 1992). Histologic analysis of DCIS cases suggests that mutations and altered gene expression events, as well as changes in chromatin and DNA content, occur predominantly in comedo DCIS (Böcker et al, 1992; Killeen et al, 1991; and, Komitowski et al, 1990), which has a rapid rate of local invasion and progression to metastasis. Thus, there are presently no reliable marker genes for non-comedo DCIS (NCDCIS, hereafter).

Cancer in humans appears to be a multi-step process which involves progression from pre-malignant to malignant to metastatic disease which ultimately kills the patient. Epidemiologic studies in humans have established that certain pathologic conditions are "premalignant" because they are associated with increased risk of malignancy. There is precedent for detecting and eliminating pre-invasive lesions as a cancer prevention strategy: dysplasia and carcinoma in-situ of the uterine cervix are examples of pre-malignancies which have been successfully employed in the prevention of cervical cancer by cytologic screening methods. Unfortunately, because the breast cannot be sampled as readily as cervix, the development of screening methods for breast pre-malignancy involves more complex approaches than cytomorphologic screening now currently employed to detect cervical cancer.

Pre-malignant breast disease is also characterized by an apparent morphological progression from atypical hyperplasias, to carcinoma in-situ (pre-invasive cancer) to invasive cancer which ultimately spreads and metastasizes resulting in the death of the patient. Careful histologic examination of breast biopsies has demonstrated intermediate stages which have acquired some of these characteristics but not others. Detailed epidemiological studies have established that different morphologic lesions progress at different rates, varying from atypical hyperplasia (with a low risk) to comedo ductal carcinoma-in-situ which progresses to invasive cancer in a high percentage of patients (London et al, 1991; Page et al, 1982; Page et al, 1985; Page et al, 1991; and Page et al, 1978). Family history is also an important risk factor in the development of breast cancer and increases the relative risk of these pre-malignant lesions (Dupont et al, 1985; Dupont et al, 1993; and, London et al, 1991). Of particular interest is non-comedo carcinomaoin-situ which is associated with a greater than ten-fold increased relative risk of breast cancer compared to control groups (Ottesen et al, 1992; Page et al, 1982). Two other reasons besides an increased relative risk support the concept that DCIS is pre-malignant: 1) When breast cancer occurs in these patients it regularly occurs in the same region of the same breast where the DCIS was found; and 2) DCIS is frequently present in tissue adjacent to invasive breast cancer (Ottesen et al, 1992; Schwartz et al, 1992). For these reasons DCIS very likely represents a rate-limiting step in the development of invasive breast cancer in women.

DCIS (sometimes called intraductal carcinoma) is a group of lesions in which the cells have grown to completely fill the duct with patterns similar to invasive cancer, but do not invade outside the duct or show metastases at presentation. DCIS occurs in two forms: comedo DCIS and non-comedo DCIS. Comedo DCIS is often a grossly palpable lesion which was probably considered "cancer" in the 19th and early 20th century and progresses to cancer (without definitive therapy) in at least 50% of patients within three years (Ottesen et al, 1992; Page et al, 1982). Most of the molecular alterations which have been reported in pre-malignant breast disease have been observed in cases of comedo DCIS (Poller et al, 1993; Radford et al, 1993; and, Tsuda et al, 1993). Non-comedo DCIS is detected by microscopic analysis of breast aspirates or biopsies and is associated with a 10 fold increased risk of breast cancer, which corresponds to a 25-30% absolute risk of breast cancer within 15 years (Ottesen et al, 1992; Page et al, 1982; and, Ward et al, 1992).

Widespread application of mammography has changed the relative incidence of comedo and non-comedo DCIS such that NCDCIS now represents the predominant form of DCIS diagnosed in the United States (Ottesen et al, 1992; Page et al, 1982; and Pierce et al, 1992). Both forms of DCIS generally recur as invasive cancer at the same site as the pre-malignant lesion (without definitive therapy). The precursor lesions to DCIS are probably atypical ductal hyperplasia and proliferative disease without atypia which are associated with lower rates of breast cancer development, but show further increased risk when associated with a family history of breast cancer (Dupont et al, 1985; Dupont et al, 1989; Dupont et al, 1993; Lawrence, 1990; London et al, 1991; Page et al, 1982; Page et al, 1985; Page et al, 1991; Page et al, 1978; Simpson et al, 1992; Solin et al, 1991; Swain, 1992; Weed et al, 1990).

What is needed, then, is a sensitive method of detection and diagnosis of breast cancer when the cancerous cells are still in the pre-invasive stage. To illustrate the usefulness in early breast cancer detection of a marker gene and its encoded protein, consider the dramatic impact that prostate specific antigen has had on early stage prostate cancer. This method of early detection and diagnosis of breast cancer is presently lacking in the prior art.

SUMMARY OF THE INVENTION

Epidemiologic studies have established that NCDCIS of the breast is associated with a ten-fold increased risk of breast cancer (absolute risk of 25-30%). It seems likely that this pre-invasive lesion is a determinate precursor of breast cancer because the subsequent development of breast cancer is regularly in the same region of the same breast in which the NCDCIS lesion was found. Important aspects of the present invention concern isolated DNA segments and those isolated DNA segments inserted into recombinant vectors encoding differentially expressed marker genes in abnormal tissue, specifically in NCDCIS, as compared with those expressed in normal tissue, and the creation and use of recombinant host cells through the application of DNA technology, which express these differentially expressed marker genes (Sambrook et al, 1989).

Because there are no cell lines or animal models which clearly display known characteristics of pre-invasive breast disease, human breast tissue samples are essential for studying pre-invasive breast disease. Using human tissue samples, we subsequently have developed a method for cDNA cloning from histologically identified lesions in human breast biopsies. We have used this method to clone genes which are differentially expressed in pre-invasive breast lesions such as NCDCIS lesions as compared to genes expressed in normal tissue. The differentially expressed genes detected in pre-invasive breast cancer are called marker genes. Identification of marker genes for pre-invasive breast disease provides improved methods for detection and diagnosis of pre-invasive breast cancer tissue, and further provides marker genes for studies of the molecular events involved in progression from pre-invasive to malignant breast disease.

Analysis of marker gene expression in NCDCIS presents the advantage that cancerous breast tissue at that stage is non-invasive. Detection and diagnosis of NCDCIS by means of differentially expressed marker genes compared to the same marker genes in normal breast tissue, would allow a greater ability to detect, prevent and treat the disease before it becomes invasive and metastasizes. The stage or intermediate condition of NCDCIS is a particularly good candidate for early intervention because it is 1) prior to any invasion and thus prior to any threat to life; 2) it is followed by invasive carcinoma in over 30% of cases if only treated by biopsy; and, 3) there is a long "window" of opportunity (4-8 years) approximately before invasive neoplasia occurs. Thus, NCDCIS is an ideal target for early diagnosis. While these morphologically defined intermediate endpoints have been widely accepted, progress in defining the molecular correlates of these lesions has been hampered by an inability to identify and sample them in a manner which would allow the application of molecular techniques.

Frozen tissue blocks from breast biopsies were used to construct and screen cDNA libraries prepared from NCDCIS tissue, normal breast tissue, breast cancer tissue, and normal human breast epithelial cells. Several cDNAs which were differentially expressed in human DCIS epithelial cells compared to normal breast epithelial cells were cloned and sequenced. One gene which is differentially expressed is the M2 subunit of RibRed which is expressed at low levels in human breast epithelial cells but at higher levels in 4 out of 5 DCIS tissue samples. It is presumed that the altered morphologic appearance and determinant biologic behavior of DCIS results from altered expression of genes (such as RibRed) which is important in the induction of breast cancer in humans.

This invention, therefore, provides a method of detecting and diagnosing pre-invasive breast cancer by analyzing marker genes which are differentially expressed in non-comedo DCIS cells. Histopathologic studies have demonstrated that these morphologic patterns in breast tissue lead to invasive breast cancer in at least 20-30% of patients. The present method analyzes gene expression in normal, pre-malignant and malignant breast biopsies; and, it allows simultaneous comparison and cloning of marker genes which are differentially expressed in pre-invasive breast cancer. These marker genes can then be used as probes to develop other diagnostic tests for the early detection of pre-invasive breast cancer.

The present invention concerns DNA segments, isolatable from both normal and abnormal human breast tissue, which are free from total genomic DNA. The isolated DCIS-1 protein product is the regulatory element of the RibRed enzyme. This and all other isolatable DNA segments which are differentially expressed in preinvasive breast cancer can be used in the detection, diagnosis and treatment of breast cancer in its earliest and most easily treatable stages. As used herein, the term "abnormal tissue" refers to pre-invasive and invasive breast cancer tissue, as exemplified by collected samples of non-comedo or comedo DCIS tissues.

As used herein, the term "DNA segment" refers to a DNA molecule which has been isolated free of total genomic DNA of a particular species. Therefore, a DNA segment encoding a differentially expressed protein (as measured by the expression of mRNA) in abnormal tissue refers to a DNA segment which contains differentially expressed-coding sequences in abnormal tissue as compared to those expressed in normal tissue, yet is isolated away from, or purified free from, total genomic DNA of Homo sapiens sapiens. Included within the term "DNA segment", are DNA segments and smaller fragments of such segments, and also recombinant vectors, including, for example, plasmids, cosmids, phage, viruses, and the like.

Similarly, a DNA segment comprising an isolated or purified differentially expressed gene refers to a DNA segment including differentially expressed coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, any differentially expressed marker gene forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode differentially expressed genes in pre-invasive breast cancer, each which includes within its amino acid sequence an amino acid sequence in accordance with SEQ ID NO:1, SEQ ID NO:2, SEQ ID NO:3, SEQ ID NO:4, SEQ ID NO:5, SEQ ID NO:6, or SEQ ID NO:7, all seq id no:s 1–7 are derived from non-comedo DCIS samples from Homo sapiens sapiens. In other particular embodiments, the invention concerns isolated DNA segments and recombinant vectors incorporating DNA sequences which encode the M2 subunit of human RibRed that includes within its amino acid sequence the similar amino acid sequence of hamster RibRed corresponding to the M2 subunit of hamster RibRed.

In certain embodiments, the invention concerns isolated DNA segments and recombinant vectors which partially or wholly encode a protein or peptide that includes within its amino acid sequence an amino acid sequence essentially as partially or wholly encoded, respectively, by SEQ ID NO:1, SEQ ID NO:2, SEQ ID NO:3, SEQ ID NO:4, SEQ ID NO:5, SEQ ID NO:6, or SEQ ID NO:7. Naturally, where the DNA segment or vector encodes a full length differentially expressed protein, or is intended for use in expressing the differentially expressed protein, the most preferred sequences are those which are essentially as set forth in SEQ ID NO:1, SEQ ID NO:2, SEQ ID NO:3, SEQ ID NO:4, SEQ ID NO:5, SEQ ID NO:6, or SEQ ID NO:7 and which encode a protein that exhibits differential expression, e.g., as may be determined by the differential display or differential sequencing assay, as disclosed herein.

The term "a sequence essentially as set forth in SEQ ID NO:1, SEQ ID NO:2, SEQ ID NO:3, SEQ ID NO:4, SEQ ID NO:5, SEQ ID NO:6, or SEQ ID NO:7" means that the sequence substantially corresponds to a portion of SEQ ID NO:1, SEQ ID NO:2, SEQ ID NO:3, SEQ ID NO:4, SEQ ID NO:5, SEQ ID NO:6, or SEQ ID NO:7, respectively, and has relatively few nucleotides which are not identical to, or a biologically functional equivalent of, the nucleotides of the respective SEQ ID NO:1, SEQ ID NO:2, SEQ ID NO:3, SEQ ID NO:4, SEQ ID NO:5, SEQ ID NO:6, or SEQ ID NO:7. The term "biologically functional equivalent" is well understood in the art and is further defined in detail below. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:1, SEQ ID NO:2, SEQ ID NO:3, SEQ ID NO:4, SEQ ID NO:5, SEQ ID NO:6, or SEQ ID NO:7 will be sequences which are "essentially as set forth in SEQ ID NO:1, SEQ ID NO:2, SEQ ID NO:3, SEQ ID NO:4, SEQ ID NO:5, SEQ ID NO:6, or SEQ ID NO:7", respectively.

In certain other embodiments, the invention concerns isolated DNA segments and recombinant vectors that include within their sequence a nucleic acid sequence essentially as set forth in SEQ ID NO:1, SEQ ID NO:2, SEQ ID NO:3, SEQ ID NO:4, SEQ ID NO:5, SEQ ID NO:6, and SEQ ID NO:7. The term "essentially as set forth in SEQ ID NO:1, SEQ ID NO:2, SEQ ID NO:3, SEQ ID NO:4, SEQ ID NO:5, SEQ ID NO:6, and SEQ ID NO:7" is used in the same sense as described above and means that the nucleic acid sequence substantially corresponds to a portion of SEQ ID NO:1, SEQ ID NO:2, SEQ ID NO:3, SEQ ID NO:4, SEQ ID NO:5, SEQ ID NO:6, and SEQ ID NO:7, respectively, and has relatively few codons which are not identical, or functionally equivalent, to the codons of SEQ ID NO:1, SEQ ID NO:2, SEQ ID NO:3, SEQ ID NO:4, SEQ ID NO:5, SEQ ID NO:6, and SEQ ID NO:7, respectively. Again, DNA segments which encode proteins exhibiting differential expression will be most preferred. The term "functionally equivalent codon" is used herein to refer to codons that encode the same amino acid, such as the six codons for arginine or serine, and also refers to codons that encode biologically equivalent amino acids (see FIG. 8).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 20% and about 50%; or more preferably, between about 50% and about 70%; or even more preferably, between about 70% and about 99%; of nucleotides which are identical to the nucleotides of SEQ ID NO:1, SEQ ID NO:2, SEQ ID NO:3, SEQ ID NO:4, SEQ ID NO:5, SEQ ID NO:6, and SEQ ID NO:7 will be sequences which are "essentially as set forth in SEQ ID NO:1, SEQ ID NO:2, SEQ ID NO:3, SEQ ID NO:4, SEQ ID NO:5, SEQ ID NO:6, and SEQ ID NO:7", respectively. Sequences which are essentially the same as those set forth in SEQ ID NO:1, SEQ ID NO:2, SEQ ID NO:3, SEQ ID NO:4, SEQ ID NO:5, SEQ ID NO:6, and SEQ ID NO:7 may also be functionally defined as sequences which are capable of hybridizing to a nucleic acid segment containing the complement of SEQ ID NO:1, SEQ ID NO:2, SEQ ID NO:3, SEQ ID NO:4, SEQ ID NO:5, SEQ ID NO:6, and SEQ ID NO:7, respectively, under relatively stringent conditions. Suitable relatively stringent hybridization conditions will be well known to those of skill in the art (Sambrook et al, 1989).

It is also important to understand the molecular events which lead to progression from pre-invasive to invasive breast cancer. Breast cancer is a disease that is presumed to involve a series of genetic alterations that confer increasing growth independence and metastatic capability on somatic cells. Identifying the molecular events that lead to the initial development of a neoplasm is therefore critical to understanding the fundamental mechanisms by which tumors arise and to the selection of optimal targets for gene therapy and chemopreventive agents. As intermediate endpoints in neoplastic development, some pre-malignant breast lesions represent important, and possibly rate-limiting steps in the progression of human breast cancer, and careful epidemiological studies have established the relative risk for breast cancer development for specific histologic lesions. In particular, invasive breast cancer develops in the region of the previous biopsy site in at least 25–30% of patients following diagnosis of non-comedo DCIS providing strong evidence that this pre-malignant lesion is a determinant event in breast cancer progression. While these morphologically defined intermediate endpoints have been widely accepted, progress in defining the molecular correlates of these lesions has been hampered by an inability to identify and sample them in a manner which would allow the application of molecular techniques.

The present invention includes a comparison of gene expression between multiple breast tissue biopsy samples as a means to identify differentially expressed genes in pre-malignant breast disease compared with normal breast tissue. These genetic markers should be extremely useful reagents for early diagnosis of breast cancer, and for the delineation of molecular events in progression of breast cancer.

Identification of gene markers which are expressed in the majority of pre-invasive breast cancer tissue samples involves cDNA library preparation from both normal and abnormal tissue. This is followed by either a modified differential display method or a differential screening method to identify differential expression of genes which is subsequently confirmed by RT-PCR, nuclease protection assays and in situ hybridization of DCIS tissue RNA and control tissue RNAs (Sambrook et al, 1989). Use of genetic engineering methods can bias the screening to specifically identify genes whose encoded proteins are secreted or are present at the cell surface, in order to find proteins which will be useful markers for diagnostic blood tests (secreted proteins) or for diagnostic imaging studies (cell surface proteins).

Thus, the method of the present invention begins with the collection of at least one tissue sample by a microscopically-directed collection step in which a punch biopsy is obtained exclusively from abnormal tissue which exhibits histological or cytological characteristics of pre-invasive breast cancer. Preferably, the sample site will be an isolatable tissue structure, such as ductal epithelial cells from pre-invasive breast cancer tissue. The mRNA is purified from the sample. Then, a cDNA library is prepared from the mRNA purified from the abnormal tissue sample (Sambrook et al, 1989).

A normal tissue sample is then obtained from the patient, using a sample site from an area of tissue which does not exhibit histological or cytological characteristics of pre-invasive cancer. A cDNA library is also prepared from this normal tissue sample.

The abnormal tissue cDNA library can then be compared with the normal tissue cDNA library by differential display or differential screening to determine whether the expression of at least one marker gene in the abnormal tissue sample is different from the expression of the same marker gene in the normal tissue sample.

Further diagnostic steps can be added to the method by cloning the marker gene using sequence-based amplification to create a cloned marker gene which can then be DNA-sequenced in order to derive the protein sequence. The protein sequence is then used to generate antibodies which will recognize these proteins by antibody recognition of the antigen. The presence of the antibody-recognized antigen can then be detected by means of conventional medical diagnostic tests.

An object of the present invention, then, is to provide a method of early detection of pre-invasive breast cancer in human tissue.

It is a further object of this invention to identify early marker genes for pre-invasive breast disease which can be used in screening methods for early pre-invasive breast cancer.

Finally, it is an object of this invention to produce a cDNA library from pre-invasive breast cancer tissue resulting in a permanent genetic sample of that pre-invasive breast cancer tissue.

| List of Abbreviations | |
|---|---|
| TPA | Phorbol 12-myristate 13-acetate |
| MCF-7 | An immortalized cell line derived from a metastasis of human breast cancer |
| HMEC | A primary (non-immortalized) cell line derived from breast epithelial cells obtained during reduction mammoplasty |
| DCIS | Ductal Carcinoma-in-situ |
| NCDC | Non-Comedo Ductal Carcinoma in situ |
| cDNA | Complementary DNA obtained from an RNA template |
| DNA | Deoxyribonucleic Acid |
| RT-PCR | Reverse Transcriptase-Polymerase Chain Reaction |
| RibRed | Ribonucleotide Reductase |

BRIEF DESCRIPTION OF THE FIGURES

The file of this patent contains at least one drawing executed in color. copies of this patent with color drawing(s) will be provided by the Patent and Trademark Office upon request and payment of the necessary fee.

FIG. 1 shows Table I which describes anatomic lesion types in the human breast with pre-malignant implication.

FIG. 2 shows a model for pre-malignant conditions, highlighting magnitude of risk for progression to clinical malignancy.

FIG. 3 contains color photos of DCIS tissue, before (upper left panel) and after microscopically-directed excisional punch biopsy (upper right panel). The lower panels show tissue samples of normal breast tissue (lower left panel), and invasive breast cancer (lower right panel).

FIG. 4 shows expression of collagen III mRNA in tissue mRNA samples, analyzed by RNase protection assay methods.

FIG. 5 shows differential display of cDNAs obtained from patient tissue samples and controls.

FIG. 6 shows a comparison of the sequence between DCIS-1 and the human and hamster genes.

FIG. 7 shows expression of DCIS-1 mRNA in tissue mRNA samples analyzed by RNase protection assay as described in the legend to FIG. 4.

FIG. 8 is Table II which displays the genetic code.

FIG. 9 is a Table which lists differentially expressed marker genes.

DESCRIPTION OF THE PREFERRED EMBODIMENT

For the purposes of the subsequent description, the following definitions will be used: Nucleic acid sequences which are "complementary" are those which are capable of base-pairing according to the standard Watson-Crick complementarity rules. That is, that the larger purines will always base pair with the smaller pyrimidines to form only combinations of Guanine paired with Cytosine (G:C) and Adenine paired with either Thymine (A:T) in the case of DNA or Adenine paired with Uracil (A:U) in the case of RNA.

"Hybridization techniques" refer to molecular biological techniques which involve the binding or hybridization of a probe to complementary sequences in a polynucleotide. Included among these techniques are northern blot analysis, southern blot analysis, nuclease protection assay, etc.

"Hybridization" and "binding" in the context of probes and denatured DNA are used interchangeably. Probes which are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must be the degree of complementarity and/or the longer the probe.

"Probe" refers to an oligonucleotide or short fragment of DNA designed to be sufficiently complementary to a sequence in a denatured nucleic acid to be probed and to be bound under selected stringency conditions.

"Label" refers to a modification to the probe nucleic acid that enables the experimenter to identify the labeled nucleic acid in the presence of unlabeled nucleic acid. Most commonly, this is the replacement of one or more atoms with radioactive isotopes. However, other labels include covalently attached chromophores, fluorescent moeities, enzymes, antigens, groups with specific reactivity, chemiluminescent moeities, and electrochemically detectable moeities, etc.

"Marker gene" refers to any gene selected for detection which displays differential expression in abnormal tissue as opposed to normal tissue. It is also referred to as a differentially expressed gene.

"Marker protein" refers to any protein encoded by a "marker gene" which protein displays differential expression in abnormal tissue as opposed to normal tissue.

"Tissuemizer" describes a tissue homogenization probe.

"Abnormal tissue" refers to pathologic tissue which displays cytologic, histologic and other defining and derivative features which differ from that of normal tissue. This includes in the case of abnormal breast tissue, among others, pre-invasive and invasive neoplasms.

"Normal tissue" refers to tissue which does not display any pathologic traits.

"PCR technique" describes a method of gene amplification which involves sequenced-based hybridization of primers to specific genes within a DNA sample (or library) and subsequent amplification involving multiple rounds of annealing, elongation and denaturation using a heat-stable DNA polymerase.

"RT-PCR" is an abbreviation for reverse transcriptase-polymerase chain reaction. Subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase produced by *Thermus aquaticus* for its amplification action.

"Microscopically-directed" refers to the method of tissue sampling by which the tissue sampled is viewed under a microscope during the sampling of that tissue such that the sampling is precisely limited to a given tissue type, as the investigator requires. Specifically, it is a collection step which involves the use of a punch biopsy instrument. This surgical instrument is stereotactically manually-directed to harvest exclusively from abnormal tissue which exhibits histologic or cytologic characteristics of pre-invasive cancer. The harvest is correlated with a companion slide, stained to recognize the target tissue.

"Differential display" describes a method in which expressed genes are compared between samples using low stringency PCR with random oligonucleotide primers.

"Differential screening" describes a method in which genes within cDNA libraries are compared between two samples by differential hybridization of cDNAs to probes prepared from each library.

"Nuclease protection assay" refers to a method of RNA quantitation which employs strand specific nucleases to identify specific RNAs by detection of duplexes.

"Differential expression" describes the phenomenon of differential genetic expression seen in abnormal tissue in comparison to that seen in normal tissue.

"Isolatable tissue structure" refers to a tissue structure which when visualized microscopically or otherwise is able to be isolated from other different surrounding tissue types.

"In situ hybridization of RNA" refers to the use of labeled DNA probes employed in conjunction with histological sections on which RNA is present and with which the labeled probe can hybridize allowing an investigator to visualize the location of the specific RNA within the cell.

"Comedo DCIS cells" refers to cells comprising an in situ lesion with the combined features of highest grade DCIS.

"Non-comedo DCIS cells" refers to cells of DCIS lesions without comedo features.

"Cloning" describes separation and isolation of single genes.

"Sequencing" describes the determination of the specific order of nucleic acids in a gene or polynucleotide.

The present invention provides a method for detecting and diagnosing cancer by analyzing marker genes which are differentially expressed in early, pre-invasive breast cancer, specifically in non-comedo DCIS cells. Our histopathologic studies have demonstrated that certain morphologic patterns in breast tissue are pre-malignant, leading to invasive breast cancer in at least 20–30% of patients. We have developed a new method for analyzing gene expression in normal, pre-malignant and malignant breast biopsies which allows simultaneous comparison and cloning of marker genes which are differentially expressed in pre-invasive breast cancer. These marker genes (which appear as differentially expressed genes in pre-invasive breast cancer) can be used as probes to develop diagnostic tests for the early detection of pre-invasive breast cancer (Sambrook, 1989).

The present invention thus comprises a method of identification of marker genes which are expressed in the majority of pre-invasive breast cancer tissue samples. It involves cDNA library preparation followed by a modified differential display method. Use of genetic engineering methods (Sambrook, 1989) can bias the screening to specifically identify genes whose encoded proteins are secreted or are present at the cell surface, in order to find proteins which will be useful markers for diagnostic blood tests (secreted proteins) or for diagnostic imaging studies (cell surface proteins).

Naturally, the present invention also encompasses DNA segments which are complementary, or essentially complementary, to the sequence set forth in SEQ ID NO:1, SEQ ID NO:2, SEQ ID NO:3, SEQ ID NO:4, SEQ ID NO:5, SEQ ID NO:6, and SEQ ID NO:7. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1, SEQ ID NO:2, SEQ ID NO:3, SEQ ID NO:4, SEQ ID NO:5, SEQ ID NO:6, and SEQ ID NO:7 under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, SEQ ID NO:2, SEQ ID NO:3, SEQ ID NO:4, SEQ ID NO:5, SEQ ID NO:6, and SEQ ID NO:7, such as about 10 nucleotides, and which are up to 10,000 or 5,000 base pairs in length, with segments of 500 being preferred in most cases. DNA segments with total lengths of about 1,000, 500, 200, 100 and about 50 base pairs in length are also contemplated to be useful.

It will also be understood that this invention is not limited to the particular nucleic acid and amino acid sequences of SEQ ID NO:1, SEQ ID NO:2, SEQ ID NO:3, SEQ ID NO:4, SEQ ID NO:5, SEQ ID NO:6, and SEQ ID NO:7. Recombinant vectors and isolated DNA segments may therefore variously include the differentially expressed coding regions themselves, coding regions bearing selected alterations or modifications in the basic coding region, or they may encode larger polypeptides which nevertheless include differentially expressed-coding regions or may encode biologically functional equivalent proteins or peptides which have variant amino acids sequences.

The DNA segments of the present invention encompass biologically functional equivalent differentially expressed proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test site-directed mutants or others in order to examine carcinogenic activity of the differentially expressed marker genes at the molecular level.

If desired, one may also prepare fusion proteins and peptides, e.g., where the differentially expressed marker gene coding regions are aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with a RIBRED gene, e.g., in human cells, as may be obtained by isolating the 5' noncoding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a differentially expressed marker gene in its natural environment. Such promoters may include MMTV promoters normally associated with other genes, and/or promoters isolated from any other bacterial, viral, eukaryotic, or mammalian cell. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to appropriate bacterial promoters.

As mentioned above, in connection with expression embodiments to prepare recombinant differentially expressed marker gene encoded proteins and peptides, it is contemplated that longer DNA segments will most often be used, with DNA segments encoding the entire differentially expressed protein or subunit being most preferred. However, it will be appreciated that the use of shorter DNA segments to direct the expression of differentially expressed peptides or epitopic core regions, such as may be used to generate anti-marker protein antibodies, also falls within the scope of the invention (Harlow et al, 1988).

DNA segments which encode peptide antigens from about 15 to about 50 amino acids in length, or more preferably, from about 15 to about 30 amino acids in length are contemplated to be particularly useful. The C terminus of proteins provide an excellent region for peptide antigen recognition (Harlow et al, 1988). DNA segments encoding peptides will generally have a minimum coding length in the order of about 45 to about 150, or to about 90 nucleotides. DNA segments encoding partial length peptides may have a minimum coding length in the order of about 50 nucleotides for a polypeptide in accordance with seq id no:3, or about 264 nucleotides for a polypeptide in accordance with SEQ ID NO: 1.

In addition to their use in directing the expression of the differentially expressed marker proteins, the nucleic acid sequences disclosed herein also have a variety of other uses. For example, they also have utility as probes or primers in nucleic acid hybridization embodiments. As such, it is contemplated that oligonucleotide fragments corresponding to the sequences of SEQ ID NO:1, SEQ ID NO:2, SEQ ID NO:3, SEQ ID NO:4, SEQ ID NO:5, SEQ ID NO:6, and SEQ ID NO:7 for stretches of between about 10 to 15 nucleotides and about 20 to 30 nucleotides will find particular utility. Longer complementary sequences, e.g., those of about 40, 50, 100, 200, 500, 1000, and even up to full length sequences of about 2,000 nucleotides in length, will also be of use in certain embodiments.

The ability of such nucleic acid probes to specifically hybridize to differentially expressed marker gene sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having stretches of 20, 30, 50, or even of 500 nucleotides or so, complementary to SEQ ID NO:1, SEQ ID NO:2, SEQ ID NO:3, SEQ ID NO:4, SEQ ID NO:5, SEQ ID NO:6, and SEQ ID NO:7 are particularly contemplated as hybridization probes for use in, e.g., Southern and Northern blotting. This would allow differentially expressed structural or regulatory genes to be analyzed, both in patients and sample tissue from pre-invasive and invasive breast tissue. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, but larger complementary stretches of up to about 300 nucleotides may be used, according to the length complementary sequences one wishes to detect.

Nucleic Acid Hybridization

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired.

Hybridization probes may be selected from any portion of any of the sequences disclosed herein. All that is required is to review the sequences set forth in SEQ ID NO:1, SEQ ID NO:2, SEQ ID NO:3, SEQ ID NO:4, SEQ ID NO:5, SEQ ID NO:6, and SEQ ID NO:7 and to select any continuous portion of one of the sequences, from about 10 nucleotides in length up to and including the full length sequence, that one wishes to utilise as a probe or primer. The choice of probe and primer sequences may be governed by various factors, such as, by way of example only, one may which to employ primers from towards the termini of the total sequence, or from the ends of the functional domain-encoding sequences, in order to amplify further DNA; one may employ probes corresponding to the entire DNA, or to the 5' region, to clone marker-type genes from other species or to clone further marker-like or homologous genes from any species including human; and one may employ randomly selected, wild-type and mutant probes or primers with sequences centered around the RibRed M2 subunit encoding sequence to screen DNA samples for differentially expressed levels of RibRed; such as to identify human subjects which may be expressing differential levels of RibRed and thus may be susceptible to breast cancer.

The process of selecting and preparing a nucleic acid segment which includes a sequence from within SEQ ID NO:1, SEQ ID NO:2, SEQ ID NO:3, SEQ ID NO:4, SEQ ID NO:5, SEQ ID NO:6, and SEQ ID NO:7 may alternatively be described as "preparing a nucleic acid fragment". Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR technology of U.S. Pat. No. 4,683,202 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of differentially expressed marker genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating specific differentially expressed marker genes.

Of course, for some applications, for example, where one desires to prepare mutants employing a mutant primer strand hybridized to an underlying template or where one seeks to isolate marker gene sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label. (Sambrook et al, 1989).

In a preferred embodiment of the method, certain preliminary procedures are necessary to prepare the sample tissue and the probes before the detection of differential expression of marker genes in abnormal tissue as compared to that in normal tissue can be accomplished.

SAMPLE PREPARATION

RNA purification

RNA was isolated from frozen tissue samples by mincing of microdisected frozen tissue fragments with a razor blade and then adding 800 microliter of 5.6M guanidinium to increase mixing, followed by a 30 second microcentrifuge centrifugation at 14,000 rpm to remove particulate matter. The supernatant was then removed and the viscosity was reduced by multiple aspirations through a 22 gauge needle and then 200 ul of chloroform was added and the sample was incubated on ice for 15 minutes (during this time the sample was vortexed multiple times). Following incubation with chloroform, the sample was centrifuged for 15 minutes at 14,000 rpm and the aqueous layer was removed and ethanol precipitated. This extraction method produces RNA which is primarily derived from cells of epithelial origin. In order to obtain RNA samples which presumably includes RNA derived from these stromal cells; the particulate material (remaining in the pellet from the 30 second centrifugation) was homogenized with a tissuemizer, washed with PBS, treated with collagenase at 37° C. for 30 minutes, sonicareal, extracted with phenol/chloroform and ethanol precipitated.

cDNA libraries were constructed in lambda phage using polyA-selected mRNA from the following samples; cultured human breast epithelial cells, tissue from three reduction mammoplasty patients, tissue from three DCIS patients, and tissue from one DCIS patient (patient #10) that showed a focus of microinvasion adjacent to an area of DCIS. Multiple punches were needed to obtain sufficient RNA for polyA selection and library construction. 200 ug of total RNA was obtained by pooling 20 punches from normal breast tissue (reduction mammoplasty samples) and 5–8 punches from DCIS lesions, presumably reflecting the greater cellularity of the DCIS samples. cDNA libraries were constructed by first and second strand cDNA synthesis followed by the addition of directional synthetic linkers (ZAP-cDNA Synthesis Kit, Stratagene, La Jolla, Calif.). The Xho I-Eco RI linkered cDNA was then ligated into lambda arms, packaged with packaging extracts, and then used to infect XL1-blue bacteria resulting in cDNA libraries.

PROBE PREPARATION

The collagen III probe employed for nuclease protection assays was constructed by subcloning the 208 bp Hinc II-Pst I fragment from the 3' untranslated region of the human type III procollagen gene into pGem4Z. This region of the human procollagen III gene was obtained by PCR amplification of published sequence (Ala-Kokko et al, 1989) followed by restriction with Hinc II and Pst I. For a control probe to assure equal loading and recovery of RNA, we used a T7 polymerase-generated probe for human glyceraldehyde phosphate dehydrogenase (GADP) which protects a 140 bp Sac I-Xba I fragment; (a generous gift from Janice Nigro, Vanderbilt University). Probe DCIS-1 was generated by linearizing the rescued plasmid with Pvu II, which should generate a 200 bp protected fragment. RNase protection assays were performed with 1 ug of unselected RNA and the above-cited probes using the methods we have reported previously (Holt, 1993).

Differential Display-based cloning of cDNAs:

Rescued cDNA library samples were used as templates for low stringency PCR with the either a pair of 25 bp primers or an anchored 14 bp primer paired with a random 25 bp primer. Random 25 bp primers were generated by a computer-based algorithm (Jotte and Holt, unpublished). Samples were denatured for two minutes at 95° C. followed by 40 cycles, each cycle consisting of denaturation for 1 minute at 94° C., annealing for 2 minutes at 25° C., and extension for 1 minute at 72° C. The samples were then run on an 6% non-denaturing polyacrylamide gel, which was dried and autoradiographed. Specific bands were excised then reamplified with the same primers used for their generation. Specificity was confirmed on 6% polyacrylamide gel, and samples were purified by ethanol precipitation of the remainder of the PCR reaction. Fragments were then individually cloned into Srfl cut vectors by standard methods using PCR-Script™MSK(+) Cloning Kit (Stratagene, LaJolla, Calif.) and then sequenced.

EXAMPLE 1

Studies showing Increased Risk of Breast Cancer in Patients with DCIS

Since the 1970's, studies of pre-invasive lesions associated with the development of breast cancer have been undertaken in an attempt to refine histologic and cytologic criteria for the hyperplastic lesions analogous to those of the uterine cervix and colon. Because of the availability of tissue from breast biopsies done many years previously, cohorts of women who underwent breast biopsies 15 to 20 years ago, can be studied to determine the risk for development of breast cancer attributable to specific lesions. Many concurrent studies evaluating lesions associated with cancer at time of cancer diagnosis led the way in pointing out lesions of potential interest (Wellings et al, 1975). Hopefully, these intermediate stages in cancer development will serve to provide indicators of breast cancer development sufficiently precise to guide prevention and intervention strategies (Weed et al, 1990; Lippman et al, 1990). Such intermediate elements prior to the development of metastatic capable cancers also provide the opportunity to define the molecular biology of these elements. Studies of the development of preinvasive breast disease have provided insight into different types of lesions with different implications for breast cancer risk and the process of carcinogenesis (See FIG. 1). Pre-invasive breast disease is herewith defined to be any reproducibly defined condition which confers an elevated risk of breast cancer approaching double that of the general population (Komitowski et al, 1990). The specifically-defined atypical hyperplasias and lobular carcinoma in situ confer relative risks of four to ten times that of the general population. This risk is for carcinoma to develop anywhere in either breast (Page et al, 1985; Page et al, 1991). The statistical significance of these observations have regularly been <0.0001. Thus, absolute risk figures of 10–20% likelihood of developing into invasive carcinoma in 10 to 15 years arise. DCIS is a very special element in this story because the magnitude of risk is as high as any other condition noted (P<0.00005), but remarkably, the developing invasive cancer is in the same site in the same breast. This local recurrence and evolution to invasiveness marks these lesions as determinate precursors of invasive breast cancer (Betsill et al, 1978; Page et al, 1982). These figures are for the type of DCIS which has become detected very commonly since the advent of mammography, the small and NCDCIS variety. It is likely that the comedo DCIS variety indicates a much greater risk, often presenting as larger lesions, and treated regularly by mastectomy in the past 50 years making follow-up studies impossible (FIG. 1). The precision of histopathologic diagnosis in this area as noted in Table I (shown in FIG. 1) was most convincingly confirmed in a large, prospective study (London et al, 1991). There has also been a recent review of the reproducibility of the assignment of diagnosis by a panel of pathologists (Schnitt et al, 1992). The precision has been fostered by combining histologic pattern criteria with cytologic and extent of lesion criteria. Classic surgical pathology criteria were predominantly derived from histologic pattern only. A further point of relevance to the importance of these histopathologically defined lesions of pre-malignancy in the breast is the relationship to familiality. A family history of breast cancer in a first degree relatives confers about a doubling of breast cancer risk. However, women with the atypical hyperplasias at biopsy and a family history of breast cancer are at 9–10 times the risk of developing invasive breast cancer as the general population (Dupont et al, 1985; Dupont et al, 1989).

Careful consideration of all of the above-mentioned epidemiologic data has led to the following model for progression from generalized pre-malignant lesions to determinant lesions to invasive cancer. FIG. 2 shows this model for the induction and progression of pre-invasive breast disease based on study of the Vanderbilt cohort (Dupont et al, 1985) of more than 10,000 breast biopsies (follow-up rate 85%; median time of 17 years; 135 women developed breast cancer).

EXAMPLE 2

Identification of genes which are differentially expressed in DCIS Construction of cDNA libraries from DCIS lesions In order to study differential gene expression in DCIS, we collected cases of NCDCIS. The diagnosis of DCIS is made on histomorphologic grounds based on architectural, cytologic, and occasionally extent criteria. NCDCIS lacks comedo features and consists of microscopic intraductal lesions which fill and extend the duct, contain rigid internal architecture, and often have hyperchromatic and monomorphic nuclei.

Study of non-comedo DCIS for differential marker gene expression indicates the diagnostic utility of comparison of marker gene expression in these tissues. Although the morbidity and mortality of breast cancer clearly results from invasion and metastasis, the development of breast cancer is clearly significant in its early stages for two basic reasons:

1) The molecular changes will presumably be simpler in early lesions than in later lesions which may have acquired numerous mutations or "hits"; and
2) Successful prevention strategies may require attacking cancer before it develops the capacity to invade or metastasize.

Non-comedo DCIS is the earliest determinant lesion which recurs locally as invasive cancer. Although comedo DCIS may be technically easier to study because the tumors are larger, its aggressiveness and the presence of numerous genetic alterations (such as p53 and erbB2) suggest that it may have advanced beyond the earliest stages of carcinogenesis. The commercial utility of a method for prevention of cancer is clear. In order to study differential gene expression in DCIS, breast tissue with extensive microscopic non-comedo DCIS was identified and banked in a frozen state. cDNA libraries were constructed from mRNA isolated from frozen sections of DCIS lesions. Tissue samples from patients with mammographic results consistent with DCIS were cryostat frozen and a definitive diagnosis was made by the histopathologic criteria which we have described (Jensen et al, Submitted for publication; Holt et al, In press).

Control mRNA was obtained from frozen tissue samples obtained from reduction mammoplasties and from cultured human breast epithelial cells. Because non-comedo DCIS is a microscopic lesion, we had to microlocalize regions of DCIS in biopsy samples. To accomplish this we prepared frozen sections in which we located regions of DCIS and then employed a 2 mm punch to obtain an abnormal tissue sample only from those regions that contained DCIS. This selective harvesting was accomplished by carefully aligning the frozen section slide with the frozen tissue block and identifying areas of interest. The harvest of the appropriate area was then confirmed with a repeat frozen section. A similar approach was used to isolate mRNA from lobules of normal breast in samples collected from a reduction mammoplasty. Prior studies have shown that breast lobules are approximately 2.5 mm in diameter, thus the 2 mm punch provided a well-tailored excision. This microlocation and collection step, in which abnormal tissue samples are collected from an isolatable tissue structure, was performed with extreme care and was absolutely crucial to the success of these studies. Contamination by normal breast epithelial cells or by breast stromal cells would clearly negatively skew the differential screening approach. If the punch biopsy did not cleanly excise DCIS without contamination by other cell types or tissues then the sample was not used for mRNA isolation (Jensen et al, Submitted for publication). FIG. 3 contains color photos of DCIS (abnormal) tissue, before (upper left panel) and after excisional punch biopsy (upper fight panel). The lower panels show tissue samples of normal breast tissue (lower left panel), and invasive breast cancer (lower fight panel).

Following microlocation punch harvesting of the frozen tissue, RNA was isolated, purified, and employed to construct cDNA libraries. RNA was isolated following mincing of tissue in 5.6M guanidinium isothiocyanate and 40% phenol, centrifugation to remove particulate matter, viscosity reduction by repeated aspiration through a 22 gauge needle, chloroform extraction and ethanol precipitation. In most samples there was particulate matter resistant to guanidinium-phenol extraction that was white in color and fibrous in appearance and was presumed to represent breast stroma. This stromal material was sparse in DCIS samples but abundant in samples obtained from normal breast tissue derived from reduction mammoplasties. The stromal material was minced with a tissuemizer, washed with PBS, treated with collagenase at 37° C. for 30 minutes, sonicated, extracted with phenol/chloroform and ethanol precipitated. 200 ug of total RNA was obtained by pooling 20 punches from normal breast tissue (reduction mammoplasty samples) and 5–8 punches from DCIS lesions, presumably reflecting the greater cellularity of the DCIS samples. All libraries had greater than 50% inserts and contained between 2×10⁶ and 7×10⁷ phage recombinants with an average insert size varying between 500 and 1000 base pairs.

EXAMPLE 3

Development of an extraction method which produces breast epithelial RNA _p It was necessary that tissue samples not be contaminated by non-epithelial stromal cells. Such contamination would complicate efforts to compare gene expression between samples. In order to test the extent of stromal contamination of the mRNA samples, we determined the level of expression of collagen III mRNA by an RNase protection assay. RNase protection assays were employed in these and subsequent studies because it is a quantitative method and can be performed on small amounts of unselected RNA. Collagen III mRNA was identified in the presumed stromal fraction of the normal breast tissue and to a lesser extent in the microinvasive breast cancer sample, but no expression of collagen III was detected in the DCIS samples which were subsequently employed for cDNA library construction. FIG. 4 compares expression in NL 2 and #10CA with other patient samples and NL1 to determine collagen III expression.

Expression of Collagen III mRNA in tissue mRNA samples was analyzed by RNase protection assay by methods we have reported previously (Holt, 1993). One µg of mRNA was hybridized with two labeled RNA probes: a T7 polymerase-generated probe for human glyceraldehyde phosphate dehydrogenase (GADP) which protects a 140 bp Sac I-Xba I fragment; and a T7 polymerase-generated probe which protects a 208 bp Hinc II-Pst I fragment from the 3' untranslated region of the human type III procollagen gene (Coll III) obtained by PCR subcloning of the published sequence (Ala-Kokko et al, 1991). RNA samples were labeled as follows: NL1 is RNA from cultured human breast epithelial cells (Hammond et al, 1984), NL2 is RNA from normal breast tissue, NL3 is RNA derived from the fibrous stromal fraction of breast tissue as described (Jensen et al, Submitted for publication), NL4 is another sample from normal breast tissue. This is described in greater detail above. #12, #8, #4, #6, and #10 are from patient samples with DCIS. Sample #10CA is RNA obtained from the small focus of microinvasion shown in FIG. 3. Con is a control sample using tRNA.

EXAMPLE 4

Screening of cDNA libraries

Following successful testing which demonstrated that stromal contamination was not a problem, cDNA libraries were constructed in lambda phage using polyA-selected mRNA from the following samples: cultured human breast epithelial cells, tissue from three reduction mammoplasty patients, tissue from three DCIS patients, and tissue from one DCIS patient (patient #10) that showed a small focus of invasion adjacent to an area of DCIS. Multiple punches were needed to obtain sufficient RNA for polyA selection and library construction. Selective handling of tissue was accomplished.

Comparison of gene expression between samples was performed by either differential screening or a modification of differential display (Liang et al, 1992a; Liang et al, 1992b; Saiki et al, 1988; Melton et al, 1984). Plasmid DNA was prepared from the cDNA libraries following helper phage rescue and screened by two independent methods. FIG. 5 below shows the results of differential display comparing cDNAs of several patient DCIS samples with cDNA obtained from normal breast epithelial cells and an early invasive cancer. Although few genes shown in this Figure are differentially expressed in the majority of samples with DCIS, the heterogeneity of gene expression in patient samples is seen.

The differential display method (Liang et al, 1992a and 1992b) allows simultaneous comparison of multiple tissue samples. Initial studies using this method (reverse transcriptase followed by PCR) were unsatisfactory because of unwanted amplification of contaminating DNA in tissue samples and the small size of many of the fragments identified by display. To circumvent some of these problems, we have attempted to combine the advantages of cDNA library screening with the advantages of differential display by:

1) Constructing cDNA libraries from the tissue mRNA samples;
2) Performing differential display on the plasmid DNA prepared from the cDNA libraries;
3) Subcloning the fragments identified by differential display;
4) Using the subcloned fragment as a probe to clone the cDNA from the appropriate library.

EXAMPLE 5

Identification of a gene (RibRed) which is differentially expressed in multiple NCDCIS cases Employing these methods, 10 differentially expressed clones were identified and the seven that showed the greatest difference in expression between multiple samples were further characterized by DNA sequencing. Comparison of the sequenced clones with GenBank demonstrated that six of the clones are apparently unique sequences (although further DNA sequencing is necessary); but that one of the clones (here termed DCIS-1 and described in Sequence Listing No. 1) showed 90% homology to the previously cloned hamster gene encoding the M2 subunit of ribonucleotide reductase (Pavloff et al, 1992; Hurta et al, 1991; Hurta et al, 1991). Although human M2 ribonucleotide reductase has been cloned previously, comparison of the hamster cDNA sequence with our clone and with the prior human clone indicates that DCIS-1 is homologous to an alternatively poly-adenylated form of the human ribonucleotide reductase which has not been cloned previously. FIG. 6 shows a comparison of the sequence between DCIS-1 and the human and hamster genes.

Because of our concern that different patients may have differential gene expression which is idiosyncratic (or related to morphological differences in biopsy appearance) and not necessarily related to the induction or progression of DCIS, we simultaneously analyzed gene expression in multiple DCIS samples compared to multiple control samples. We constructed cDNA libraries from the following samples:

1) Cultured HMEC epithelial cells;
2) Reduction mammoplasty: 11 year old with virginal hyperplasia;
3) Reduction mammoplasty: 28 year old patient;
4) Reduction mammoplasty: 35 year old patient;
5) DCIS patient #12;
6) DCIS patient #8;
7) DCIS patient #10;
8) DCIS patient #10 form an area of invasive cancer adjacent to DCIS;

In addition an area of invasive cancer adjacent to DCIS;

In addition to the samples we employed to construct cDNA libraries shown above, we also obtained frozen tissue samples from 7 more DCIS patients, 2 cellular fibroadenoma samples, and samples of "usual hyperplasia" and atypical hyperplasia. Because the DCIS clones were identified by cloning methods which include selection and amplification, it was important to confirm by nuclease protection assays that the genes were differentially expressed in the original unselected, unamplified RNA samples (FIG. 7). This approach allowed identification of a human gene similar to the hamster RibRed gene (coding for the M2 subunit) and 7 other human genes as genes which are differentially expressed in a majority of cases of DCIS in human breast tissue. The table of differentially expressed genes lists the genes which have been identified as differentially expressed genes in DCIS tissue samples as compared to that in normal tissue (FIG. 9).

EXAMPLE 6

Methods for studying potential use of differentially expressed genes for diagnostic screening One advantage of the differential display method is that it allows comparison of multiple tissue samples of pre-invasive or invasive breast cancer. For example, use of this method has successfully demonstrated that the M2 subunit ribonucleotide reductase gene is differentially expressed in 4 out of 5 pre-invasive breast cancer tissue samples. It is significant that the M2 subunit is involved in the regulation of the ribonucleotide reductase gene and is found to be over-expressed in abnormal tissue samples.

Identification of differentially expressed genes may lead to discovery of genes which are potentially useful for breast cancer screening. Of particular interest are genes whose expression is restricted to breast epithelial cells and whose gene products are secreted. Screening for secreted proteins is possible by using the known hydrophobic sequences which encode leader sequences as one primer for differential display. The identification of secreted proteins which are specific for early breast pre-malignancy (or even early invasive cancer) would provide an important tool for early breast cancer screening programs. If a differentially expressed gene has not been cloned previously (or if details of its expression are unknown or uncertain) then nuclease protection assays or Northern blots can be performed on RNA prepared from tissue samples from a variety of tissues to determine if expression of this gene is restricted to breast. If necessary cDNA libraries prepared from other tissues can be added to the differential display screen as a way to identify only those genes which are expressed in early breast cancer and, in addition, are only expressed in breast tissue.

Once differentially expressed genes have been initially characterized for expression in pre-malignant and malignant breast disease, antibodies to the protein products of potentially useful genes can be developed and employed for immunohistochemistry (Harlow et al, 1988). This will provide an additional test to determine whether the expression of this gene is restricted to the breast. Subsequently, these antibodies will be used to detect the presence of this protein present in the blood of patients with pre-invasive and/or invasive cancer. By assaying for serum protein levels in the same patients who exhibited elevated expression of the gene in their tissue samples it will be possible to determine whether a gene product is being secreted into the blood.

REFERENCE LIST

Abendroth, C. S., H. H. Wang, et al. 1991. Comparative features of carcinoma in situ and atypical ductal hyperplasia of the breast on fine-needle aspiration biopsy specimens. Am J Clin Pathol 96(5): 654–659.

Ala-Kokko,L., S. Kontusaari, C. T. Baldwin, H. Kuivaniemi, D. J. Prockop. 1991. Structure of cDNA clones coding for the entire preproalpha I (III) chain of human type III procollagen. Biochemical Journal 260, 509–516.

Allred, D. C., G. M. Clark, et al. 1992. Overexpression of HER-2/neu and its relationship with other prognostic factors change during the progression of in situ to invasive breast cancer. Hum Pathol 23(9): 974–979.

Betsill, W. L., Jr., P. P. Rosen, P. H. Lieberman, and G. F. Robbins. 1978. Intraductal carcinoma. Long term follow-up after biopsy only. J.A.M.A. 239:1863–1867.

Böcker, W., B. Bier, et al. 1992. An immunohistochemical study of the breast using antibodies to basal and luminal keratins, alpha-smooth muscle actin, vimentin, collagen IV and laminin. Part II: Epitheliosis and ductal carcinoma in situ. Virchows Arch A Pathol Anat Hispathol 421: 323–330.

Callahan R., C. S. Cropp, G. R. Merlo, D. S. Liscia, A. P. M. Cappa, and R. Lidereau. 1992. Somatic mutations and human breast cancer. Cancer 69: 1582–86.

Carter D., R. R. L. Smith. 1977. Carcinoma in situ of the breast. Cancer 40:1189–1193.

Cheickh M. B., P. Rouanet, G. Louason, P. Jeanteur, and C. Theillet. 1992. An attempt to define sets of cooperating genetic alterations in human breast cancer. Int. J. Cancer 51:542–547.

Chen L.-C., W Kurisu, B.-M. Ljung, E. S. Goldman, Dmorre II, and H. S. Smith. 1992. Heterogeneity for allelic loss in human breast cancer. JNCI 84:506–510.

Dupont, W. D., Parl F. F., Hartmann W. H., Brinton L. A., Winfield A. C., Worrell J. A., Schuyler P. A., Plummer W. D.: Breast cancer risk associated with proliferative breast disease and atypical hyperplasia. Cancer 71:1258–1265, 1993.

Dupont W. D., and D. L. Page. 1985. Risk factors for breast cancer in women with proliferative breast disease. N. Engl. J. Med. 312:146–151.

Dupont W. D., D. L. Page, L. W. Rogers, and F. F. Parl. 1989. Influence of exogenous estrogens, proliferative breast disease, and other variables on breast cancer risk. Cancer 63:948–957.

Fentiman, I. S. 1992. Ductal carcinoma in situ. B. M. J. 304: 1261–1262.

Fisher, E. R. and R. Siderit .1992. Value of cytometric analysis for distinction of intraductal carcinoma of the breast. Breast Cancer Res Treat 21: 165–172.

Hammond S. L., R. G. Ham, and M. R. Stampfer. 1984. Serum-free growth of human mammary epithelial cells: rapid clonal growth in defined medium and extended serial passage with pituitary extract. Proc. Natl. Acad. Sci. U.S.A. 81:5435–5439.

Harlow E., D. Lane. 1988. Antibodies. A Laboratory Manual. Cold Spring Harbor Laboratory Press.

Holt J. T., R. A. Jensen, and D. L. Page. Histopatholoy: Old Principles and new methods. 1994. Cancer Surveys. In Press.

Holt, J. T. Antisense rescue defines specialized and generalized functional domains for c-fos protein. 1993. Molecular and Cellular Biology 13, 3821–3830.

Hurta, R. A. R., J. A. Wright. 1991. Alteration in the activity and regulation of mammalian ribonucleotide reductase by a DNA damaging agent. Journal of Biological Chemistry 267, 7066–7071.

Hurta, R. A. R., S. K. Samuel, A. H. Greenberg, J. A. Wright. 1991. Early induction of ribonucleotide reductase gene expression by TGF-beta1 in malignant Ras transformed cell lines. Journal of Biological Chemistry 266, 24097–24100.

Jensen, R. A., D. L. Page, and J. T. Holt. Identification of genes expressed in pre-malignant breast disease by microscopically-directed cloning. Submitted for publication.

Killeen, J. L. and H. Namiki .1991. DNA analysis of ductal carcinoma in situ of the breast: A comparison with histologic features. Cancer 68: 2602–2607.

Komitowski D., and C. Janson. 1990. Quantitative features of chromatin structure in the prognosis of breast cancer. Cancer 65:2725–2730.

Lawrence, G. 1991. Evaluation of treatment options for ductal carcinoma in situ of the breast. Arch Surg 126: 1541–1541.

Lennington, W. J., R. A. Jensen, L. W. Dalton, and D. L. Page. Ductal carcinoma in situ of the breast. Cancer 73: 118–124, 1994.

Liang P., and A. B. Pardee. 1992. Differential display of eukaryotic mRNA by means of the polymerase chain reaction. Science 257:967–971.

Liang P., L. Averboukh, K. Keyomarsi, R. Sager, and A. B. Pardee. 1992. Differential display and cloning of messenger RNAs from human breast cancers versus mammary epithelial cells. Cancer 52:6966–6968.

Lippman S. M., J. S. Lee, R. Lotan, W. Hittelman, M. J. Wargovich, and W. K. Hong. 1990. Biomarkers as intermediate endpoints in chemoprevention trials. JNCI 82:555–560.

London S. J., J. L. Connolly, S. J. Schnitt, and G. A. Colditz. 1991. A prospective study of benign breast disease and risk of breast cancer. J.A.M.A. 267:941–944.

Maguire, H. J., M. E. Hellman, et al. 1992. Expression of c-erbB-2 in in situ and in adjacent invasive ductal adenocarcinomas of the female breast. Pathobiology 60: 117–121.

Melton, D. A., D. A. Krieg, M. R. Rebagliati, T. Flaniatis, K. Zinn, and M. R. Green. 1984. SP6 RNA polymerase. Nucleic. Acid. Res. 12: 7035–7056.

Onesen, G. L., H. P. Graversen, et al. 1992. Ductal carcinoma in sire of the female breast: Short-term results of a prospective nationwide study. Am J Surg Pathol 16: 1183–1196.

Page D. L., W. D. Dupont, L. W. Rogers, and M. Landenberger. 1982. Intraductal carcinoma. Follow-up after biopsy only. Cancer 49:751–758.

Page D. L., W. D. Dupont, L. W. Rogers, and M. S. Rados. 1985. Atypical hyperplastic lesions of the female breast. A long term follow-up study. cancer 55:2698–2708.

Page D. L., T. E. Kidd, W. D. Dupont, J. F. Simpson, and L. W. Rogers. 1991. Lobular neoplasia of the breast: higher risk for subsequent invasion predicted by more extensive disease. Hum Pathol. 22:1232–1239.

Page D. L., R. Vander Zwaag, L. W. Rogers, L. T. Williams, W. E. Alker, and W. H. Hartman. 1978. Relation between component parts of fibrocystic disease complex and breast cancer. J. Natl. Cancer Inst. 61:1055–1063.

Pavloff, N., D. Rivard, S. Masson, S. H. Sheri, A. M. Mes-Masson. 1992.Sequence analysis of the large and small subunits of human ribonucleotide reductase. DNA Sequence 2, 227–234.

Pierce, S. M., S. J. Schnitt, et al. 1992. What to do about mammographically detected ductal carcinoma in situ? Cancer 70: 2576–2578.

Poller, D. N., C. E. Hutchings, et al. 1992. p53 Protein expression in human breast carcinoma: Relationship to expression of epidermal growth factor receptor, c-erbB-2 protein overexpression, and oestrogen receptor. Br J Cancer 66: 583–588.

Poller, D. N., E. C. Roberts, J. A. Bell, C. W. Elston, R. W. Blamey, and I. O. Ellis. p53 expression in mammary ductal carcinoma in situ: relationship to immunohistochemical expression of estrogen receptor and cerbB2 protein. Human Pathology 1993, 24:463–468.

Posner, M. C. and N. Wolmark 1992. Non-invasive breast carcinoma. Breast Cancer Res Treat 21: 155–164.

Radford D. M., K. Fair, A. M. Thompson, J. H. Ritter, M. Holt, T. Steinbrueck, W. Wallace, Wells S. A. Jr., and H. R. Donis-Keller. Allelic loss on chromosome 17 in ductal carcinoma in situ of the breast. Cancer Res 1993, 53:2947–2950.

Saiki, R. K., D. H. Gelfand, S. Stoffel, S. J. Scharf, R. Higuchi, G. T. Horn, K. B. Mullis, and H. A. Erlich. 1988. Primer directed enzymatic amplification of DNA with a thermostable DNA polymerase. Science 239:487–491.

Sambrook J., E. F. Fritsch, T. Maniatis. 1989. Molecular Cloning Laboratory Manual, 2d Edition. Cold Spring Harbor Laboratory Press.

Sanchez L. M., F. Vizoso, I. Diez-Itza, C. Lopez-Otin. 1992. Cancer Res 32:95–100.

Schnitt, S. J., J. L. Connolly, F. A. Tavassoli, et al. 1992. Interobserver reproducibility in the diagnosis of ductal proliferative breast lesions using standardized criteria. Am. J. Surg. Pathol. 16:1133–1143.

Schwartz, G. F., G. C. Finkel, et al. 1992. Subclinical ductal carcinoma in situ of the breast: Treatment by local excision and surveillance alone. Cancer 70: 2468–2474.

Simpson, T., R. C. Thirlby, et al. 1992. Surgical treatment of ductal carcinoma in situ of the breast: 10- to 20-year follow-up. Arch Surg 127: 468–472.

Solin, L. J., A. Recht, et al. 1991. Ten-year results of breast-conserving surgery and definitive irradiation for intraductal carcinoma (ductal carcinoma in sire) of the breast. Cancer 68: 2337–2344.

Swain, S. M. 1992. Ductal carcinoma in situ. Cancer Invest 10: 443–454.

Tsuda H., K. Iwaya, T. Fukutomi, S. Hirohashi. p53 mutations and c-erbB2 amplification in intraductal and invasive breast carcinomas of high histologic grade. Jpn J Cancer Res 1993, 84:394–401.

Ward, B. A., C. F. McKhann, et al. 1992.Ten-year follow-up of breast carcinoma in situ in Connecticut. Arch Surg 12: 1392–1395.

Weed D. L., P. Greenwald, and J. W. Cullera. 1990. The future of cancer prevention and control. Semin. Oncol. 17:504–509.

Wellings S. R., H. M. Jensen, and R. G. Marcum. 1975. An atlas of subgross pathology of the human breast with special reference to possible precancerous lesions. J. Natl. Cancer Inst. 55:231–273.

Thus, although there have been described particular embodiments of the present invention of a new and useful "Method of Detection and Diagnosis of Pre-invasive Breast Cancer", it is not intended that such embodiments be construed as limitations upon the scope of this invention except as set forth in the following claims. It will be apparent to those skilled in the art that many changes and modifications may be made without departing from the invention in its broader aspects. For example, the above described techniques may be used in the diagnosis of other diseases and detection of differential genetic expression from microscopically-directed tissue samples of pathologic tissue. The production of a cDNA library produced as a result of the differential expression of genes in pathologic tissue in comparison to normal tissue provides the opportunity for further diagnostic capabilities. Further, although there have been described certain experimental conditions used in the preferred embodiment, it is not intended that such conditions be construed as limitations upon the scope of this invention except as set forth in the following claims.

---

What is claimed is:

1. A method for detecting differential expression of at least one marker gene in DCIS (ductal carcinoma situ) pre-invasive cancerous breast tissue, said method comprising the steps of:

(a) obtaining an abnormal breast tissue sample which exhibits histological or cytological characteristics of pre-invasive breast cancer by a step wherein epithelial cells are included and non-epithelial cells are excluded during the collection of said abnormal breast tissue sample;

(b) isolating mRNA from said abnormal breast tissue sample;

(c) preparing one or more abnormal breast tissue cDNA libraries from said mRNA isolated from said abnormal breast tissue sample;

(d) obtaining a normal breast tissue sample from humans either with or without disease, which does not exhibit histological or cytological characteristics of pre-invasive breast cancer by a step wherein epithelial cells are included and non-epithelial cells are excluded during the collection of said normal breast tissue sample;

(e) preparing one or more normal breast tissue cDNA libraries from said normal breast tissue sample as in (b) and (c); and (f) comparing said abnormal breast tissue cDNA library with said normal tissue cDNA library to detect the expression of at least one marker gene in said abnormal breast tissue sample which is different from the expression of said marker gene in said normal breast tissue sample, whereby differential, expression of at least one marker gene in DCIS pre-invasive breast cancer tissue is detected.

2. The method according to claim 1 wherein said collection step is microscopically-directed.

3. The method according to claim 2 wherein the size of said abnormal tissue sample substantially conforms to an isolatable tissue structure wherein only cells exhibiting abnormal cytological or histological characteristics are collected.

4. The method according claim 3 wherein said isolatable tissue structure comprises ductal epithelial cells in DCIS pre-invasive breast cancer tissue.

5. The method according to claim 1 further comprising confirming said differential expression of said marker gene in said normal tissue sample and in said abnormal tissue sample by using a hybridization or PCR amplification technique.

6. The method according to claim 5 wherein said hybridization technique comprises RT-PCR.

7. The method according to claim 5 wherein said hybridization technique comprises nuclease protection assays.

8. The method according to claim 5 wherein said hybridization technique comprises in-situ hybridization of RNA in said abnormal tissue sample and in said normal tissue sample.

9. The method according to claim 1 wherein said abnormal cDNA library and said normal cDNA library are compared by means of differential display.

10. The method according to claim 1 wherein said abnormal cDNA library and said normal cDNA library are compared by means of differential screening.

11. The method according to claim 1, wherein said abnormal breast tissue cells are non-comedo ductal carcinoma in situ cells.

12. The method according to claim 5, wherein the primer used in the PCR amplification technique is selected from the group consisting of randomly selected primers having the sequences 5'-CGCGACGGCCGCGCGTCTGCCAGGG-3' (SEQ ID NO: 8), 5'-CTTGCGCGCATACGCACAAC-3' (SEQ ID NO: 47), 5'-AACCCTCACCCTAACCCCAA-3' (SEQ ID NO: 48), 5'-CGCCCCTGCGTTACCCTCCCCGCCG-3' (SEQ ID NO: 9), 5'-GGATGGCGTCCTGTAACCCGACGCT-3' (SEQ ID NO: 10), 5'-ACTGGGCTGTCCTGCGGTGGCGGGG-3' (SEQ ID NO: 11), 5'-CTGAGAGGTAGCCGCGCGGAGGCTG-3' (SEQ ID NO: 12), 5'-GCCTGGCCGCGACACGGATTACCGC-3' (SEQ ID NO: 13), 5'-TTAGCGCATGGTGGACCTGGAGACG-3' (SEQ ID NO: 14), 5'-TGTGGTTACGTCAGCGAAGGTAATA-3' (SEQ ID NO: 15), 5'-AGTCGCACGCATGTCACGCTCCGCC-3' (SEQ ID NO: 16), 5'-TATCCAAGCGGCAGGCTACGAGGCC-3' (SEQ ID NO: 17), 5'-GGCGCGCCCGACGGTCTGGTATCTA-3' (SEQ ID NO: 18), 5'-CTCCCTCCCCGGACTCGGGGTTAGT-3' (SEQ ID NO: 19), 5'-ATGCGGGCGGCTCGGGCCTGGTCGC-3' (SEQ ID NO: 20), 5'-CGTGAAGCCTATGCCCTCCCTCAAC-3' (SEQ ID NO: 21), 5'-GTGCCGTCGTAGCCCTTCAGCGATC-3' (SEQ ID NO: 22), 5'-GCGACACTAGGCTCCCGGAGGAGGG-3' (SEQ ID NO: 23), 5'-TGGGCCAGGCCTCCGGGCCCGGTAT-3' (SEQ ID NO: 24), 5'-CCGGAACTGCGATAGCGTCCGTCCC-3' (SEQ ID NO: 25), 5'-AGCGGACACCTGTTTCCCGAGAGCC-3' (SEQ ID NO: 26), 5'-AACGGGTGGACATCCGCCTGCCGCC-3' (SEQ ID NO: 27), 5'-TGAACCACGATGTCAATCGTCCCGA-3' (SEQ ID NO: 28), 5'-TCATCCCCGCCGAAAGACGCTCGCC-3' (SEQ ID NO: 29), 5'-ATAGGCTGCGGCACGCGCTGGGACT-3' (SEQ ID NO: 30), 5'-GACCAGGTGCGCACGAGCATGTACA-3' (SEQ ID NO: 31), 5'-AGCGTAGTCATCGGCCTTCGCGCCC-3' (SEQ ID NO: 32), 5'-GGCCCCTAGCCCAGGGTGAAGCCCA-3' (SEQ ID NO: 33), 5'-CCCAGTGCTACGGGCCGCCCCAAGC-3' (SEQ ID NO: 34), 5'-CCTTCCTGGGTTACCTGCCCTCGGG-3' (SEQ ID NO: 35), 5'-TCCGGACAGCAGCCACGCCAAGGGC-3' (SEQ ID NO: 36), 5'-ACGCGCTGGTCCACCGAGGCCTGAT-3' (SEQ ID NO: 37), 5'-CGATGCAAGGCCAGCAGCACTCGAC-3' (SEQ ID NO: 38), 5'-CCCCCGGAGCGGACCACCGGACGTG-3' (SEQ ID NO: 39), 5'-AGCGGGGAGGGATCGGGGGCCAAGC-3' (SEQ ID NO: 40), 5'-GCCTGGTGTAGGCAGGCAGCTCTTA-3' (SEQ ID NO: 41), 5'-CCACCCCTGTAGTGCGGGCTGCGAG-3' (SEQ ID NO: 42), 5'-GGAACCCGACGCCCGTCCAGGGTTC-3' (SEQ ID NO: 43), 5'-TCGGGCAGCAAGGCCGGGACGCTCC-3' (SEQ ID NO: 44), 5'-GACGGGGACGGGCTAGGTGGCTTA-3' (SEQ ID NO: 45), and 5'-CTTGTTGCCGGCGGAGAGGGCTGCC-3' (SEQ ID NO: 46).

13. The method according to claim 2, wherein said abnormal tissue sample is approximately 2 mm in diameter.

14. A diagnostic method to determine the presence of DCIS pre-invasive breast cancer using detection of a differentially expressed marker gene, wherein said diagnostic method comprises:

a) obtaining a substantially purified marker gene which is expressed to a different degree in cells from abnormal breast tissue than in cells collected from normal breast tissue;

b) isolating abnormal breast tissue from a patient, wherein epithelial cells are included and non-epithelial cells are excluded during the isolation of said abnormal breast tissue;

c) isolating normal breast tissue from a patient, wherein epithelial cells are included and non-epithelial cells are excluded during the isolation of said normal breast tissue; and d) probing nucleic acids of said abnormal breast tissue and nucleic acids of said normal breast tissue with a nucleic acid probe derived from said substantially purified marker gene using a hybridization technique to determine differential expression of said marker gene in said abnormal breast tissue compared with said normal breast tissue, said differential expression of said marker gene indicating the presence of DCIS which is pre-invasive breast cancer.

15. The method according to claim 14, wherein said substantially purified marker gene sequence comprises

| | |
|---|---|
| TTGGGAATTGGGTACGCGGGCCCCCCACTGTGCCGAATTCCTGCATGCGGGGGATCCACT | 60 |
| AGTTCAGAGCAGGCCGCCACCCGTAGGACTGGAGCTTTTGTTCGTTCCCTTTAGTGAGGG | 120 |
| TTAATTTTCGAGCTTGGCGTAATCATGGTCATAGCTGTTTCCTGTGTGAAATTGTTATCC | 180 |
| GCTCACAATTCCACACAACATACGAGCCGGAAGCATAAAAGTGTAAAGCCTGGGGTGCCT | 240 |
| AATGAGTGAGCTAACTCACATTAA | 264 [SEQ ID NO:1]. |

16. The method according to claim 14, wherein said substantially purified marker gene sequence comprises

| | |
|---|---|
| TAGCCCGGTTATCGAAATAGCCACAGCGCCTCTTCACTATCAGCAGTACGCCGCCCAGTT | 60 |
| GTACGGACACGGA | 73 (SEQ ID NO:21). |

17. The method according to claim 14, wherein said substantially purified marker gene sequence comprises

| | |
|---|---|
| TGCCCGATGTGTGTCGTACAACTGGCGCTGTGGCTGATTTCGATAA | 48 (SEQ ID NO:3). |

18. The method according to claim 14, wherein said substantially purified marker gene sequence comprises

| | |
|---|---|
| TAGCCCATGAGTTCGTGTCCGTACAACTGGGGCGCTGTGGCTGATTTCGATANNNNNAGC | 60 |
| ATCAGCCCGACG | 72 (SEQ ID NO:4). |

19. The method according to claim 14, wherein said substantially purified marker gene sequence comprises

| | |
|---|---|
| TAGCCCGGTTATCGAAATCAGCCACAGCGCCTAACTTCTGCAGAAGCCTTTGACCATCAC | 60 |
| CAGTTGTACGGACACGAACTCATC | 84 (SEQ ID NO:5) |

20. The method according to claim 14, wherein said substantially purified marker gene sequence comprises

| | |
|---|---|
| GTGGTTTCCGAAATTCCTGGGAAGGGGGGTGCTGGCGTGTGGAATTGTCGCGGCCCCTGG | 60 |
| TCTGCCGCGGCGTTTTTTGTCTACATTCGTCGTAGCTCG | 99 (SEQ ID NO:6). |

21. The method according to claim 14, wherein said substantially purified marker gene sequence comprises

| | |
|---|---|
| ATCAGCGCGCGACATTCGGGTACCCGCGCCCCCCCCTCCGTCGGAATTCCTCGAGCCGGG | 60 |
| ATCCATAGGATGTGGAGTTAGTTTTGTT | 88 (SEQ ID NO:7). |

22. A diagnostic method to determine the presence of DCIS pre-invasive breast cancer using detection of a differentially expressed marker gene, wherein said diagnostic method comprises a) obtaining a substantially purified marker gene which is expressed to a greater degree in cells from abnormal tissue than in cells collected from normal tissue;

b) isolating abnormal tissue from a patient, wherein epithelial cells are included and non-epithelial cells are excludes during the isolation of said abnormal tissue;

c) isolating mRNA from said abnormal breast tissue sample;

d) preparing one or more abnormal breast tissue cDNA libraries from said mRNA isolated from said abnormal breast tissue sample;

e) obtaining a normal breast tissue sample from humans either with or without disease, which does not exhibit histological or cytological characteristics of pre-invasive breast cancer by a collection step wherein epithelial cells are included and non-epithelial cells are excluded during the collection of said normal breast tissue sample;

f) preparing one or more normal breast tissue cDNA libraries from said normal breast tissue sample as in c) and d); and g) probing nucleic acids of the cDNA libraries of said abnormal breast tissue and of said normal breast tissue with a nucleic acid probe derived from said substantially purified marker gene using a hybridization technique to determine differential expression of said marker gene in said abnormal breast tissue compared with said normal breast tissue, said differential expression of the marker gene indicating the presence of DCIS which is pre-invasive breast cancer.

* * * * *

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 264
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v ) ORIGINAL SOURCE:
        ( A ) ORGANISM: Homo sapiens sapiens
        ( C ) INDIVIDUAL ISOLATE: sample of non-comedo DCIS
        ( D ) DEVELOPMENTAL STAGE: adult
        ( F ) TISSUE TYPE: female breast
        ( G ) CELL TYPE: ductal carcinoma in situ
        ( H ) CELL LINE: not derived from a cell line
        ( I ) ORGANELLE: no ( v i i ) IMMEDIATE SOURCE:
        ( A ) LIBRARY: cDNA library derived from human
        ( B ) CLONE: obtained from identification of differential
            gene expression ( v i i i ) POSITION IN GENOME:
        ( A ) CHROMOSOME/SEGMENT: unknown
        ( B ) MAP POSITION: unknown
        ( C ) UNITS: unknown ( i x ) FEATURE:
        ( A ) NAME/KEY: DCIS-1
        ( B ) LOCATION: GenBank accession no. L2736
        ( C ) IDENTIFICATION METHOD: microscopically-directed sampling
            and differential display
        ( D ) OTHER INFORMATION: gene encoding M2 subunit of
            humanribonucleotide reductase ( x ) PUBLICATION INFORMATION: unpublished
        ( K ) RELEVANT RESIDUES IN SEQ ID NO: 1

( x i ) SEQUENCE DESCRIPTION: SEQ ID NO:1:

```
TTGGGAATTG  GGTACGCGGG  CCCCCCACTG  TGCCGAATTC  CTGCATGCGG  GGGATCCACT      60

AGTTCAGAGC  AGGCCGCCAC  CCGTAGGACT  CCAGCTTTTG  TTCGTTCCCT  TTAGTGAGGG     120

TTAATTTTCG  AGCTTGGCGT  AATCATGGTC  ATAGCTGTTT  CCTGTGTGAA  ATTGTTATCC     180

GCTCACAATT  CCACACAACA  TACGAGCCGG  AAGCATAAAA  GTGTAAAGCC  TGGGGTGCCT     240

AATGAGTGAG  CTAACTCACA  TTAA                                              264
```

( 2 ) INFORMATION FOR SEQ ID NO:2:

( i ) SEQUENCE CHARACTERISTICS:
        ( A ) LENGTH: 73
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v ) ORIGINAL SOURCE:
    ORGANISM: Homo sapiens sapiens
    ( C ) INDIVIDUAL ISOLATE: sample of non-comedo DCIS
    ( D ) DEVELOPMENTAL STAGE: adult
    ( F ) TISSUE TYPE: female breast
    ( G ) CELL TYPE: ductal carcinoma in situ
    ( H ) CELL LINE: not derived from a cell line
    ( I ) ORGANELLE: no ( v i i ) IMMEDIATE SOURCE:
    ( A ) LIBRARY: cDNA library derived from human
    ( B ) CLONE: obtained from identification of differential
        gene expression ( v i i i ) POSITION IN GENOME:
    ( A ) CHROMOSOME/SEGMENT: unknown
    ( B ) MAP POSITION: unknown
    ( C ) UNITS: unknown ( i x ) FEATURE:
    ( A ) NAME/KEY: DCIS-2
    ( B ) LOCATION: GenBank acession no. L27637
    ( C ) IDENTIFICATION METHOD: microscopically-directed
        sampling and differential display ( x ) PUBLICATION INFORMATION: unpublished
    ( K ) RELEVANT RESIDUES IN SEQ ID NO: 2

( x i ) SEQUENCE DESCRIPTION: SEQ ID NO: 2:

```
TAGCCCGGTT ATCGAAATAG CCACAGCGCC TCTTCACTAT CAGCAGTACG CCGCCCAGTT    60
GTACGGACAC GGA                                                      73
```

( 2 ) INFORMATION FOR SEQ ID NO:3:

( i ) SEQUENCE CHARACTERISTICS:
        ( A ) LENGTH: 46
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v ) ORIGINAL SOURCE:
    ( A ) ORGANISM: Homo sapiens sapiens
    ( C ) INDIVIDUAL ISOLATE: sample of non-comedo DCIS
    ( D ) DEVELOPMENTAL STAGE: adult
    ( F ) TISSUE TYPE: female breast
    ( G ) CELL TYPE: ductal carcinoma in situ
    ( H ) CELL LINE: not derived from a cell line
    ( I ) ORGANELLE: no ( v i i ) IMMEDIATE SOURCE:
    ( A ) LIBRARY: cDNA library derived from human
    ( B ) CLONE: obtained from identification of differential
        gene expression ( v i i i ) POSITION IN GENOME:
    ( A ) CHROMOSOME/SEGMENT: unknown
    ( B ) MAP POSITION: unknown
    ( C ) UNITS: unknown ( i x ) FEATURE:
    ( A ) NAME/KEY: DCIS-3
    ( B ) LOCATION: L27638
    ( C ) IDENTIFICATION METHOD: microscopically-directed
        sampling and differential display ( x ) PUBLICATION INFORMATION: unpublished
    ( K ) RELEVANT RESIDUES IN SEQ ID NO: 3

( x i ) SEQUENCE DESCRIPTION: SEQ ID NO: 3:

TGCCCGATGT GTGTCGTACA ACTGGCGCTG TGGCTGATTT CGATAA          46

( 2 ) INFORMATION FOR SEQ ID NO:4:

( i ) SEQUENCE CHARACTERISTICS:
        ( A ) LENGTH: 72
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v ) ORIGINAL SOURCE:
        ( A ) ORGANISM: Homo sapiens sapiens
        ( C ) INDIVIDUAL ISOLATE: sample of non-comedo DCIS
        ( D ) DEVELOPMENTAL STAGE: adult
        ( F ) TISSUE TYPE: female breast
        ( G ) CELL TYPE: ductal carcinoma in situ
        ( H ) CELL LINE: not derived from a cell line
        ( I ) ORGANELLE: no ( v i i ) IMMEDIATE SOURCE:
        ( A ) LIBRARY: cDNA library derived from human
        ( B ) CLONE: obtained from identification of differential
                gene expression ( v i i i ) POSITION IN GENOME:
        ( A ) CHROMOSOME/SEGMENT: unknown
        ( B ) MAP POSITION: unknown
        ( C ) UNITS: unknown ( i x ) FEATURE:
        ( A ) NAME/KEY: DCIS-4
        ( B ) LOCATION: L27640
        ( C ) IDENTIFICATION METHOD: microscopically-directed
                sampling and differential display ( x ) PUBLICATION INFORMATION: unpublished
        ( K ) RELEVANT RESIDUES IN SEQ ID NO: 4

( x i ) SEQUENCE DESCRIPTION: SEQ ID NO: 4:

TAGCCCATGA GTTCGTGTCC GTACAACTGG GGCGCTGTGG CTGATTTCGA TANNNNNAGC          60

ATCAGCCCGA CG          72

( 2 ) INFORMATION FOR SEQ ID NO:5:

( i ) SEQUENCE CHARACTERISTICS:
        ( A ) LENGTH: 84
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v ) ORIGINAL SOURCE:
        ( A ) ORGANISM: Homo sapiens sapiens
        ( C ) INDIVIDUAL ISOLATE: sample of non-comedo DCIS
        ( D ) DEVELOPMENTAL STAGE: adult
        ( F ) TISSUE TYPE: female breast
        ( G ) CELL TYPE: ductal carcinoma in situ
        ( H ) CELL LINE: not derived from a cell line
        ( I ) ORGANELLE: no (vii) IMMEDIATE SOURCE:
 (A) LIBRARY: cDNA library derived from human
 (B) CLONE: obtained from identification of differential
  gene expression (viii) POSITION IN GENOME:
 (A) CHROMOSOME/SEGMENT: unknown
 (B) MAP POSITION: unknown
 (C) UNITS: unknown (ix) FEATURE:
 (A) NAME/KEY: DCIS-5
 (B) LOCATION: L27641
 (C) IDENTIFICATION METHOD: microscopically-directed sampling
  and differential display (x) PUBLICATION INFORMATION: unpublished
 (K) RELEVANT RESIDUES IN SEQ ID NO: 5

(xi) SEQUENCE DESCRIPTION: SEQ ID NO: 5:

```
TAGCCCGGTT ATCGAAATCA GCCACAGCGC CTAACTTCTG CAGAAGCCTT TGACCATCAC    60
CAGTTGTACG GACACGAACT CATC                                          84
```

(2) INFORMATION FOR SEQ ID NO:6:

(i) SEQUENCE CHARACTERISTICS:
  (A) LENGTH: 99
  (B) TYPE: nucleic acid
  (C) STRANDEDNESS: double
  (D) TOPOLOGY: linear (ii) MOLECULE TYPE: cDNA to mRNA (iii) HYPOTHETICAL: no (iv) ANTI-SENSE: no (v) ORIGINAL SOURCE:
  (A) ORGANISM: Homo sapiens sapiens
  (C) INDIVIDUAL ISOLATE: sample of non-comedo DCIS
  (D) DEVELOPMENTAL STAGE: adult
  (F) TISSUE TYPE: female breast
  (G) CELL TYPE: ductal carcinoma in situ
  (H) CELL LINE: not derived from a cell line
  (I) ORGANELLE: no (vii) IMMEDIATE SOURCE:
  (A) LIBRARY: cDNA library derived from human
  (B) CLONE: obtained from identification of differential
   gene expression (viii) POSITION IN GENOME:
  (A) CHROMOSOME/SEGMENT: unknown
  (B) MAP POSITION: unknown
  (C) UNITS: unknown (ix) FEATURE:
  (A) NAME/KEY: DCIS-6
  (B) LOCATION: L27642
  (C) IDENTIFICATION METHOD: microscopically-directed sampling
   and differential display (x) PUBLICATION INFORMATION: unpublished
  (K) RELEVANT RESIDUES IN SEQ ID NO: 6

(xi) SEQUENCE DESCRIPTION: SEQ ID NO: 6:

```
GTGGTTTCCG AAATTCCTGG GAAGGGGGGT GCTGGCGTGT GGAATTGTCG CGGCCCCTGG    60
TCTGCCGCGG CGTTTTTTGT CTACATTCGT CGTAGCTCG                           99
```

(2) INFORMATION FOR SEQ ID NO:7:

(i) SEQUENCE CHARACTERISTICS:
  (A) LENGTH: 88

(B) TYPE: nucleic acid
(C) STRANDEDNESS: double
(D) TOPOLOGY: linear (i i) MOLECULE TYPE: cDNA to mRNA (i i i) HYPOTHETICAL: no (i v) ANTI-SENSE: no (v) ORIGINAL SOURCE:
(A) ORGANISM: Homo sapiens sapiens
(C) INDIVIDUAL ISOLATE: sample of non-comedo DCIS
(D) DEVELOPMENTAL STAGE: adult
(F) TISSUE TYPE: female breast
(G) CELL TYPE: ductal carcinoma in situ
(H) CELL LINE: not derived from a cell line
(I) ORGANELLE: no (v i i) IMMEDIATE SOURCE:
(A) LIBRARY: cDNA library derived from human
(B) CLONE: obtained rom identification of differential gene
expression (v i i i) POSITION IN GENOME:
(A) CHROMOSOME/SEGMENT: unknown
(B) MAP POSITION: unknown
(C) UNITS: unknown (i x) FEATURE:
(A) NAME/KEY: DCIS-7
(B) LOCATION: L27643
(C) IDENTIFICATION METHOD: microscopically-directed sampling
and differential display (x) PUBLICATION INFORMATION: unpublished
(K) RELEVANT RESIDUES IN SEQ ID NO: 7

(x i) SEQUENCE DESCRIPTION: SEQ ID NO: 7:

ATCAGCGCGC GACATTCGGG TACCCGCGCC CCCCCCTCCG TCGGAATTCC TCGAGCCGGG    60

ATCCATAGGA TGTGGAGTTA GTTTTGTT    88

(2) INFORMATION FOR SEQ ID NO:8:

(i) SEQUENCE CHARACTERISTICS:
(A) LENGTH: 25
(B) TYPE: nucleic acid
(C) STRANDEDNESS: single
(D) TOPOLOGY: linear (i i) MOLECULE TYPE: DNA
(A) DESCRIPTION: PCR primer (i i i) HYPOTHETICAL: yes (i v) ANTI-SENSE: no (v) FRAGMENT TYPE: oligonucleotide (x i) SEQUENCE DESCRIPTION: SEQ ID NO: 8:

CGCGACGGCC GCGCGTCTGC CAGGG    25

(2) INFORMATION FOR SEQ ID NO:9:

(i) SEQUENCE CHARACTERISTICS:
(A) LENGTH: 25
(B) TYPE: nucleic acid
(C) STRANDEDNESS: single
(D) TOPOLOGY: linear (i i) MOLECULE TYPE: DNA
(A) DESCRIPTION: PCR primer (i i i) HYPOTHETICAL: yes ( i v ) ANTI-SENSE: no ( v ) FRAGMENT TYPE: oligonucleotide ( x i ) SEQUENCE DESCRIPTION: SEQ ID NO: 9:

CGCCCCTGCG TTACCCTCCC CGCCG        25

( 2 ) INFORMATION FOR SEQ ID NO:10:

( i ) SEQUENCE CHARACTERISTICS:
                ( A ) LENGTH: 25
                ( B ) TYPE: nucleic acid
                ( C ) STRANDEDNESS: single
                ( D ) TOPOLOGY: linear ( i i ) MOLECULE TYPE: DNA
                ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 10:

GGATGGCGTC CTGTAACCCG ACGCT        25

( 2 ) INFORMATION FOR SEQ ID NO:11:

( i ) SEQUENCE CHARACTERISTICS:
                ( A ) LENGTH: 25
                ( B ) TYPE: nucleic acid
                ( C ) STRANDEDNESS: single
                ( D ) TOPOLOGY: linear ( i i ) MOLECULE TYPE: DNA
                ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 11:

ACTGGGCTGT CCTGCGGTGG CGGGG        25

( 2 ) INFORMATION FOR SEQ ID NO:12:

( i ) SEQUENCE CHARACTERISTICS:
                ( A ) LENGTH: 25
                ( B ) TYPE: nucleic acid
                ( C ) STRANDEDNESS: single
                ( D ) TOPOLOGY: linear ( i i ) MOLECULE TYPE: DNA
                ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 12:

CTGAGAGGTA GCCGCGCGGA GGCTG        25

( 2 ) INFORMATION FOR SEQ ID NO:13:

( i ) SEQUENCE CHARACTERISTICS:
                ( A ) LENGTH: 25
                ( B ) TYPE: nucleic acid (C) STRANDEDNESS: single
(D) TOPOLOGY: linear (ii) MOLECULE TYPE: DNA
(A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 13:

GCCTGGCCGC GACACGGATT ACCGC 25

(2) INFORMATION FOR SEQ ID NO:14:

(i) SEQUENCE CHARACTERISTICS:
(A) LENGTH: 25
(B) TYPE: nucleic acid
(C) STRANDEDNESS: single
(D) TOPOLOGY: linear (ii) MOLECULE TYPE: DNA
(A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 14:

TTAGCGCATG GTGGACCTGG AGACG 25

(2) INFORMATION FOR SEQ ID NO:15:

(i) SEQUENCE CHARACTERISTICS:
(A) LENGTH: 25
(B) TYPE: nucleic acid
(C) STRANDEDNESS: single
(D) TOPOLOGY: linear (ii) MOLECULE TYPE: DNA
(A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 15:

TGTGGTTACG TCAGCGAAGG TAATA 25

(2) INFORMATION FOR SEQ ID NO:16:

(i) SEQUENCE CHARACTERISTICS:
(A) LENGTH: 25
(B) TYPE: nucleic acid
(C) STRANDEDNESS: single
(D) TOPOLOGY: linear (ii) MOLECULE TYPE: DNA
(A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 16:

AGTCGCACGC ATGTCACGCT CCGCC 25

(2) INFORMATION FOR SEQ ID NO:17:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: DNA
        (A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 17:

TATCCAAGCG GCAGGCTACG AGGCC 25

(2) INFORMATION FOR SEQ ID NO:18:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: DNA
        (A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 18:

GGCGCGCCCG ACGGTCTGGT ATCTA 25

(2) INFORMATION FOR SEQ ID NO:19:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: DNA
        (A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 19:

CTCCCTCCCC GGACTCGGGG TTAGT 25

(2) INFORMATION FOR SEQ ID NO:20:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: DNA
        (A) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 20:

ATGCGGGCGG CTCGGGCCTG GTCGC        25

( 2 ) INFORMATION FOR SEQ ID NO:21:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 21:

CGTGAAGCCT ATGCCCTCCC TCAAC        25

( 2 ) INFORMATION FOR SEQ ID NO:22:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 22:

GTGCCGTCGT AGCCCTTCAG CGATC        25

( 2 ) INFORMATION FOR SEQ ID NO:23:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 23:

GCGACACTAG GCTCCCGGAG GAGGG        25

( 2 ) INFORMATION FOR SEQ ID NO:24:

( i ) SEQUENCE CHARACTERISTICS:

(A) LENGTH: 25
(B) TYPE: nucleic acid
(C) STRANDEDNESS: single
(D) TOPOLOGY: linear (ii) MOLECULE TYPE: DNA
(A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 24:

TGGGCCAGGC CTCCGGGCCC GGTAT 25

(2) INFORMATION FOR SEQ ID NO:25:

(i) SEQUENCE CHARACTERISTICS:
(A) LENGTH: 25
(B) TYPE: nucleic acid
(C) STRANDEDNESS: single
(D) TOPOLOGY: linear (ii) MOLECULE TYPE: DNA
(A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 25:

CCGGAACTGC GATAGCGTCC GTCCC 25

(2) INFORMATION FOR SEQ ID NO:26:

(i) SEQUENCE CHARACTERISTICS:
(A) LENGTH: 25
(B) TYPE: nucleic acid
(C) STRANDEDNESS: single
(D) TOPOLOGY: linear (ii) MOLECULE TYPE: DNA
(A) DESCRIPTION: PCR primer (iii) HYPOTHETICAL: yes (iv) ANTI-SENSE: no (v) FRAGMENT TYPE: oligonucleotide (xi) SEQUENCE DESCRIPTION: SEQ ID NO: 26:

AGCGGACACC TGTTTCCCGA GAGCC 25

(2) INFORMATION FOR SEQ ID NO:27:

(i) SEQUENCE CHARACTERISTICS:
(A) LENGTH: 25
(B) TYPE: nucleic acid
(C) STRANDEDNESS: single
(D) TOPOLOGY: linear (ii) MOLECULE TYPE: DNA
(A) DESCRIPTION: PCR primer (iii) HYPOTHETICAL: yes (iv) ANTI-SENSE: no (v) FRAGMENT TYPE: oligonucleotide ( x i ) SEQUENCE DESCRIPTION: SEQ ID NO: 27:

AACGGGTGGA CATCCGCCTG CCGCC  25

( 2 ) INFORMATION FOR SEQ ID NO:28:

( i ) SEQUENCE CHARACTERISTICS:
  ( A ) LENGTH: 25
  ( B ) TYPE: nucleic acid
  ( C ) STRANDEDNESS: single
  ( D ) TOPOLOGY: linear ( i i ) MOLECULE TYPE: DNA
  ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 28:

TGAACCACGA TGTCAATCGT CCCGA  25

( 2 ) INFORMATION FOR SEQ ID NO:29:

( i ) SEQUENCE CHARACTERISTICS:
  ( A ) LENGTH: 25
  ( B ) TYPE: nucleic acid
  ( C ) STRANDEDNESS: single
  ( D ) TOPOLOGY: linear ( i i ) MOLECULE TYPE: DNA
  ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 29:

TCATCCCCGC CGAAAGACGC TCGCC  25

( 2 ) INFORMATION FOR SEQ ID NO:30:

( i ) SEQUENCE CHARACTERISTICS:
  ( A ) LENGTH: 25
  ( B ) TYPE: nucleic acid
  ( C ) STRANDEDNESS: single
  ( D ) TOPOLOGY: linear ( i i ) MOLECULE TYPE: DNA
  ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 30:

ATAGGCTGCG GCACGCGCTG GGACT  25

( 2 ) INFORMATION FOR SEQ ID NO:31:

( i ) SEQUENCE CHARACTERISTICS:
  ( A ) LENGTH: 25
  ( B ) TYPE: nucleic acid
  ( C ) STRANDEDNESS: single
  ( D ) TOPOLOGY: linear ( i i ) MOLECULE TYPE: DNA ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 31:

GACCAGGTGC GCACGAGCAT GTACA 25

( 2 ) INFORMATION FOR SEQ ID NO:32:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 32:

AGCGTAGTCA TCGGCCTTCG CGCCC 25

( 2 ) INFORMATION FOR SEQ ID NO:33:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 33:

GGCCCCTAGC CCAGGGTGAA GCCCA 25

( 2 ) INFORMATION FOR SEQ ID NO:34:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 34:

CCCAGTGCTA CGGGCCGCCC CAAGC 25

( 2 ) INFORMATION FOR SEQ ID NO:35:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: DNA
( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 35:

CCTTCCTGGG TTACCTGCCC TCGGG    25

( 2 ) INFORMATION FOR SEQ ID NO:36:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: DNA
( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 36:

TCCGGACAGC AGCCACGCCA AGGGC    25

( 2 ) INFORMATION FOR SEQ ID NO:37:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: DNA
( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 37:

ACGCGCTGGT CCACCGAGGC CTGAT    25

( 2 ) INFORMATION FOR SEQ ID NO:38:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: DNA
( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 38:

CGATGCAAGG CCAGCAGCAC TCGAC 25

( 2 ) INFORMATION FOR SEQ ID NO:39:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 39:

CCCCCGGAGC GGACCACCGG ACGTG 25

( 2 ) INFORMATION FOR SEQ ID NO:40:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 40:

AGCGGGGAGG GATCGGGGGC CAAGC 25

( 2 ) INFORMATION FOR SEQ ID NO:41:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 41:

GCCTGGTGTA GGCAGGCAGC TCTTA 25

( 2 ) INFORMATION FOR SEQ ID NO:42:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 42:

CCACCCCTGT AGTGCGGGCT GCGAG    25

( 2 ) INFORMATION FOR SEQ ID NO:43:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: DNA
( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 43:

GGAACCCGAC GCCCGTCCAG GGTTC    25

( 2 ) INFORMATION FOR SEQ ID NO:44:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: DNA
( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 44:

TCGGGCAGCA AGGCCGGGAC GCTCC    25

( 2 ) INFORMATION FOR SEQ ID NO:45:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: DNA
( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 45:

GACGGGGGAC GGGCTAGGTG GCTTA    25

( 2 ) INFORMATION FOR SEQ ID NO:46:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 46:

CTTGTTGCCG GCGGAGAGGG CTGCC    25

( 2 ) INFORMATION FOR SEQ ID NO:47:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 47:

CTTGCGCGCA TACGCACAAC    20

( 2 ) INFORMATION FOR SEQ ID NO:48:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: PCR primer ( i i i ) HYPOTHETICAL: yes ( i v ) ANTI-SENSE: no ( v ) FRAGMENT TYPE: oligonucleotide ( x i ) SEQUENCE DESCRIPTION: SEQ ID NO: 48:

AACCCTCACC CTAACCCCAA    20